(12) United States Patent
Vagle et al.

(10) Patent No.: US 9,416,360 B2
(45) Date of Patent: Aug. 16, 2016

(54) BASE MODIFIED OLIGONUCLEOTIDES

(75) Inventors: Kurt Vagle, Boulder, CO (US); Christina Dalby, Boulder, CO (US); William S. Marshall, Boulder, CO (US)

(73) Assignee: miRagen Therapeutics, Inc., Boulder, CO (US)

( * ) Notice: Subject to any disclaimer, the term of this patent is extended or adjusted under 35 U.S.C. 154(b) by 167 days.

(21) Appl. No.: 13/883,363

(22) PCT Filed: Nov. 7, 2011

(86) PCT No.: PCT/US2011/059588
§ 371 (c)(1),
(2), (4) Date: Jul. 23, 2013

(87) PCT Pub. No.: WO2012/061810
PCT Pub. Date: May 10, 2012

(65) Prior Publication Data
US 2013/0296402 A1   Nov. 7, 2013

Related U.S. Application Data

(60) Provisional application No. 61/410,672, filed on Nov. 5, 2010.

(51) Int. Cl.
*C12N 15/113* (2010.01)
*C12N 15/11* (2006.01)

(52) U.S. Cl.
CPC ............ *C12N 15/113* (2013.01); *C12N 15/111* (2013.01); *C12N 2310/141* (2013.01); *C12N 2310/321* (2013.01); *C12N 2310/322* (2013.01); *C12N 2310/3231* (2013.01); *C12N 2310/33* (2013.01); *C12N 2310/3521* (2013.01); *C12N 2310/3523* (2013.01); *C12N 2310/3527* (2013.01); *C12N 2310/3529* (2013.01); *C12N 2320/52* (2013.01)

(58) Field of Classification Search
CPC combination set(s) only.
See application file for complete search history.

(56) References Cited

U.S. PATENT DOCUMENTS

| | | | |
|---|---|---|---|
| 5,750,672 A | 5/1998 | Kempe | |
| 5,783,565 A | 7/1998 | Lee et al. | |
| 5,837,533 A | 11/1998 | Boutin | |
| 5,945,527 A | 8/1999 | Tu et al. | |
| 5,981,505 A | 11/1999 | Weiner et al. | |
| 6,127,170 A | 10/2000 | Boutin | |
| 6,217,900 B1 | 4/2001 | Ciccarelli et al. | |
| 6,268,490 B1 | 7/2001 | Imanishi et al. | |
| 6,316,198 B1 | 11/2001 | Skouv et al. | |
| 6,379,965 B1 | 4/2002 | Boutin | |
| 6,383,512 B1 | 5/2002 | Ciccarelli et al. | |
| 6,403,566 B1 | 6/2002 | Wang | |
| 6,416,510 B1 | 7/2002 | Altman et al. | |
| 6,670,461 B1 | 12/2003 | Wengel et al. | |
| 6,716,196 B2 | 4/2004 | Lesh et al. | |
| 6,747,014 B2 | 6/2004 | Teng et al. | |
| 6,770,748 B2 | 8/2004 | Imanishi et al. | |
| 6,833,361 B2 | 12/2004 | Hong et al. | |
| 6,953,466 B2 | 10/2005 | Palasis et al. | |
| 6,998,484 B2 | 2/2006 | Koch et al. | |
| 7,034,133 B2 | 4/2006 | Wengel et al. | |
| 7,202,227 B2 | 4/2007 | Boutin | |
| 7,404,969 B2 | 7/2008 | Chen et al. | |
| 7,618,947 B2 * | 11/2009 | Marcusson | C12N 15/113 435/375 |
| 8,642,751 B2 | 2/2014 | Dalby et al. | |
| 2005/0288244 A1 * | 12/2005 | Manoharan et al. | 514/44 |
| 2006/0148742 A1 | 7/2006 | Kaye et al. | |
| 2007/0060907 A1 | 3/2007 | Shapland et al. | |
| 2007/0203445 A1 | 8/2007 | Kaye et al. | |
| 2007/0213292 A1 * | 9/2007 | Stoffel | C12N 15/113 514/44 A |
| 2009/0004667 A1 * | 1/2009 | Zichi | C12Q 1/6811 435/6.11 |
| 2009/0137506 A1 | 5/2009 | Strapps et al. | |
| 2009/0226375 A1 | 9/2009 | Olson et al. | |
| 2010/0184209 A1 * | 7/2010 | Vermeulen et al. | 435/325 |
| 2011/0275794 A1 * | 11/2011 | Rohloff | C07H 21/04 536/23.1 |

FOREIGN PATENT DOCUMENTS

| | | |
|---|---|---|
| EP | 1860115 A1 | 11/2007 |
| WO | WO 98/39352 A1 | 9/1998 |
| WO | WO 03/093449 A2 | 11/2003 |
| WO | WO 2005/082440 A1 | 9/2005 |
| WO | WO 2006/089340 A3 | 8/2006 |
| WO | WO 2007/051303 A1 | 5/2007 |
| WO | WO 2007/070483 A3 | 6/2007 |
| WO | WO 2008/016924 A3 | 2/2008 |
| WO | WO 2009/012418 A2 | 1/2009 |
| WO | WO 2009/012468 A3 | 1/2009 |
| WO | WO2009012418 A2 | 1/2009 |
| WO | WO 2009/018492 A3 | 2/2009 |
| WO | WO 2009/018493 A1 | 2/2009 |
| WO | WO 2009/058818 A3 | 5/2009 |
| WO | WO 2009/062169 A2 | 5/2009 |
| WO | WO 2010/091204 A1 | 8/2010 |
| WO | WO 2010/120969 A1 | 10/2010 |
| WO | WO 2010/129672 A1 | 11/2010 |
| WO | WO 2010/129950 A1 | 11/2010 |
| WO | WO 2011/130289 A1 | 10/2011 |

OTHER PUBLICATIONS

Holmes, et al. (2005) "Syntheses and Oligonucleotide Incorporation of Nucleoside Analogues Containing Pendant Imidazolyl or Amino Functionalities—The Search for Sequence-Specific Artificial Ribonucleases." European Journal of Organic Chemistry, v.2005:5171-83.*

(Continued)

*Primary Examiner* — Jennifer McDonald
(74) *Attorney, Agent, or Firm* — Cooley LLP

(57) ABSTRACT

The present invention relates to oligonucleotides with base modified nucleosides for enhancement of binding affinity.

16 Claims, 12 Drawing Sheets

(56) References Cited

OTHER PUBLICATIONS

Ahmadian, M., et al., "A comparative study of the thermal-stability of oligodeoxynbonucleotides containing 5-substituted 2' deoxyuridines", *Nucleic Acids Res.*, 26(13):3127-3135 (1998).
Beaucage, S.L. et al., "Advances in the Synthesis of Oligonucleotides by the Phosphoramidite Approach", *Tetrahedron*, 48(12):2223-2311 (1992).
Caruthers, M. H. et al., "New Chemical Methods for Synthesizing Polynucleotides", *Nucleic Acids Research*, Symposium Series, No. 7, pp. 215-223 (1980).
Chien, K. R., "Molecular Medicine: MicroRNAs and the tell-tale heart", *Nature*, 447:389-390 (2007).
Cotton, M., et al., "2'-O-methyl, 2'-O-ethyl oligoribonucleotides and phosphorothioate oligodeoxyribonucleotides as inhibitors of the in vitro U7 snRNP-dependent mRNA processing event", *Nucleic Acids Research*, 19(10):2629-2635 (1991).
El Safadi, Y., et al., "5-Modified-2'-dU and 2'-dC as Mutagenic Anti HIV-1 Proliferation Agents: Synthesis and Activity", *J. Med. Chem.*, 53(4):1534-1545 (2010).
Gold, L. et al., "Aptamer-based multiplexed proteomic technology for biomarker discovery", 77 pages (2010) [Retrieved from the Internet Jan. 28, 2012: <http://precedings.nature.com/documents/4538/version/1/files/npre201_04538-1.pdf>].
Hashimoto et al., "Zwitterionic DNA", *J. Am.Chem.Soc.*, 115(16):7128-7134 (1993).
Koroleva, E.V., et al., "Synthesis and applications of 2-aminopyrimidine derivatives as key intermediates in chemical synthesis of biomolecules", *Russian Chemical Reviews*, 79(8):655-681 (2010).
McBbride, L.J., et al., "An investigation of several deoxynucleoside phosphoramidites useful for synthesizing deoxyoligonucleotides", *Tetrahedron Letters*, 24(3):245-248 (1983).
Ono, A., et al., "Nucleosides and nucleotides. 127. A novel and convenient post-synthetic modification method for the synthesis of oligodeoxyribonucleotides carrying amino linkers at the 5-position of 2'-deoxyuridine", *Bioorganic & Medicinal Chemistry Letters*, 4(2):361-366 (1994).
Sproat, B. S. et al., "Highly efficient chemical synthesis of 2'-O-methyloligoribonucleotides and tetrabiotinylated derivatives; novel probes that are resistant to degradation by RNA or DNA specific nucleases", *Nucleic Acids Research*, 17(9):3373-3386 (1989).
Van Rooij et al., "MicroRNAs: Powerful New Regulators of Heart Disease and Proactive Therapeutic Targets," *J. Clin. Invest.*, 117(9):2369-2376 (2007).
Vaught, J.D., et al., "Expanding the chemistry of DNA for in vitro selection", *J. Am. Chem. Soc.*, 132(12):4141-4151 (2010).
Veedu, R. N. et al., "Locked nucleic acid as a novel class of therapeutic agent," *RNA Biology*, 6(3):321-323 (2009).
Znosko et al., "NMR Studies of DNA Single Strands and DNA:RNA Hybrids with and without 1-Propynylation at C5 of Oligopyrimidines", *J. Am. Chem. Soc.*,125(20):6090-6097 (2003).
Chinese Application No. 201180064239.X, Office Action dated Jun. 9, 2014 (and English translation), 15 pages.
Chinese Application No. 201180064239.X, Search Report dated May 6, 2014, 3 pages.
PCT/US2011/059588, International Search Report mailed Mar. 21, 2012, 3 pages.
PCT/US2011/059588, Written Opinion mailed Mar. 21, 2012, 5 pages.
PCT/US2011/059588, International Preliminary Report on Patentability dated May 8, 2013, 6 pages.
European Patent Application No. 11838938.6, Examination Report dated Oct. 13, 2015.
Ito, T. et al., "Synthesis, thermal stability and resistance to enzymatic hydrolysis of the oligonucleotides containing 5-(N-aminohexyl)carbamoyl-2'-O-methyluridines", *Nucl. Acids Res.*, 31(10):2514-2523 (2003).
Juan, E.C.M. et al., "Crystal structures of DNA:DNA and DNA:RNA duplexes containing 5-(N-aminohexyl)carbamoyl-modified uracils reveal the basis for properties as antigene and antisense molecules", *Nucl. Acids Res.*, 35(6): 1969-1977 (2007).
Takanori Ito et al., "Synthesis, thermal stability and resistance to enzymatic hydrolysis of the oligonucleotides containing 5-(N-aminohexyl)carbamoyl-2'-Omethyluridines", Nucleic Acids Research, 2003, pp. 2514-2523, vol. 31, No. 10.
Ella C.M. Juan et al., "X-Ray analyses of hybrid duplexes between antisense oligonucleotides containing 5-(N-aminohexyl)carbamoyl-2'-0-methyluridine and their target RNAs", Nucleic Acids Symposium Series No. 49, 2005, pp. 65-66, Oxford University Press.
Thomas E. Lehmann et al, "Triple-Helix Formation by Pyrimidine Oligonucleotides Containing Nonnatural Nucleosides with Extended Aromatic Nucleobases: Intercalation from the major groove as a method for recognizing C: and T:A base pairs", Helvetica Chimica Acta, Sep. 22, 1997, pp. 2002-2022, vol. 80, No. 6.
B. H. Yoo, "2'-0-methyl-modified 1-19 phosphorothioate antisense oligonucleotides have reduced non-specific effects in vitro", Nucleic Acids Reserach, Mar. 26, 2004, pp. 2008-2016, vol. 32, No. 6.
EP Supplementary Search Report for EP 11838938.6, mailed Dec. 15, 2014 (7 pages).
Rooij Van Eva et al, "Toward MicroRNA-Based Therapeutics for Heart Disease the Sense in Antisense", Circulation Research, Oct. 1, 2008, pp. 919-928, vol. 103, No. 9.
Japanese Application No. 2013-537906, Office Action mailed Nov. 4, 2015 (and English translation), 11 pages.
Walldius and Jungner, "Apolipoprotein B and apolipoprotein A-I: risk indicators of coronary heart disease and targets for lipid-modifying therapy", *Journal of Internal Medicine*, 255(2): 188-205 (2004).
Judge, A.D. et al., "Design of Noninflammatory Synthetic siRNA Mediating Potent Gene Silencing in Vivo", *Molecular Therapy*, 13(3): 494-505 (2006).
Australian Application No. 2011323085, Examination Report dated Jan. 13, 2014, 2 pages.
Chinese Application No. 201180064239.X, Second Office Action dated Feb. 11, 2015 (English translation), 9 pages.
Chinese Application No. 201180064239.X, Third Office Action dated Aug. 6, 2015 (English translation), 11 pages.
Chinese Application No. 201180064239.X, Search Report mailed Feb. 11, 2015 (English translation), 2 pages.
Chinese Application No. 201180064239.X, Search Report mailed Aug. 6, 2015 (English translation), 2 pages.
EP Patent Application No. 11838938.6, Extended European Search Report dated Dec. 15, 2014.
Lehmann, T.E. et al., "Triple-Helix Formation by Pyrimidine Oligonucleotides Containing Nonnatural Nucleosides with Extended Aromatic Nucleobases: Intercalation from the major groove as a method for recognizing C•G and T•A base pairs", *Helvetica Chimica Acta*, 80(6): 2002-2022 (1997).
Sinha et al., "A new synthesis of oligodeoxynucleoside methylphosphonates on control pore glass polymer support using phosphite approach", *Tetrahedron Letters*, 24(9): 5843-5846 (1983).
Van Rooij et al., "Toward MicroRNA-Based Therapeutics for Heart Disease—the sense in antisense", *Circulation Research*, 103(9): 919-928 (2008).
Yoo, B.H. et al., "2'-O-methyl-modified phosphorothioate antisense oligonucleotides have reduced non-specific effects in vitro", *Nucleic Acids Research*, 32(6): 2008-2016 (2004).

* cited by examiner

FIGURE 1

| RNA U Modification | Structure | $T_m$ Enhance (°C/Residue) (=dT in DNA) | RNA U Modification | Structure | $T_m$ Enhance (°C/Residue) |
|---|---|---|---|---|---|
| Benzyl (+ 2'-OMe) | (benzyl) | +2.5 (±0.5) | 3-Propyl imidazole (+ 2'-OMe) | (propyl imidazole) | +4.5 (±1) |
| C-6 (+ 2'-OMe) | (C6 chain) | +2 (±0.5) | Propyl Morpholine (+ 2'-OMe) | (propyl morpholine) | +5.3 (±1) |
| C-8 (+ 2'-OMe) | (C8 chain) | No change (on 3' end) | Propyl Dimethyl amino (+ 2'-OMe) | (propyl dimethyl amino) | +5 (±1) |
| 2-Ethyl-2-Methyl-Imidazole (+ 2'-OMe) | (2-ethyl-2-methyl imidazole) | +5 (±1) | Ethyl Dimethyl amino (+ 2'-OMe) | (ethyl dimethyl amino) | Not Measured |

FIGURE 5

| Compound | Mods | Base Mod Pattern | Tm |
|---|---|---|---|
| M10673 | DNA | dCdTdTdTdTdG+ACdTdCdGdTdCdTdA | 46.2 |
| M10158 | 2'OMe | mCmUmUmUmUmCmUmCmGmUmCmGmUmCmUmA | 64.1 |
| M10101 | LNA/DNA (9) | lCdTdTdTdTdGtCdTlClGdTlCdTlTlA | 86.7 |
| M10583 | LNA T (9) | mClTlTlTlTlmGmClTmCmGlTmClTlTmA | 87.1 |
| Lipophilic Modifications | | | |
| M10708 | Bn-U (9) | mC+U+U+U+U+UmGmC+UmCmG+UmC+U+UmA | 68.0 |
| M10713 | C-6-U (9) | mC+U+U+U+U+UmGmC+UmCmG+UmC+U+UmA | 63.1 |
| Imidazole Modifications | | | |
| M10711 | 3-Pr-Im-U (9) | mC+U+U+U+U+UmGmC+UmCmG+UmC+U+UmA | 81.7 |
| M10712 | 2-Et-2Me-Im-U (9) | mC+U+U+U+U+UmGmC+UmCmG+UmC+U+UmA | 77.2 |
| M10768 | 2-Et-2Me-Im-U (4) | mC+U+UmUmUmUmGmCmUmCmGmUmC+U+UmA | 71.9 |
| Dimethylamine Modification | | | |
| M10772 | PrDMA U (9) | mC+U+U+U+U+UmGmC+UmCmG+UmC+U+UmA | 80.0 |
| M10774 | PrDMA U (4) | mC+U+UmUmUmUmGmCmUmCmGmUmC+U+UmA | 73.1 |

FIGURE 5 (continued)

| Morpholine Modification | | | |
|---|---|---|---|
| M-10876 | PrMorph-U (9) | mC+U+U+U+U+UmGmC+UmCmG+UmC+U+UmA | 76.5 |
| M-10877 | iC18,9 PrMorph-U | mC+U+U+U+U+UmGmC+UmCmG+UmC+UyUmA | 76.2 |
| M-10878 | PrMorph-U (4) | mC+U+UmUmUmUmGmCmUmCmGmUmC+U+UmA | 71.9 |
| M-10881 | PrMorph-U (5) | mCmUmU+U+U+UmGmC+UmCmG+UmCmUmUmA | 77.8 |

BASE MODIFIED OLIGONUCLEOTIDES

This application is the U.S. national stage of international patent application PCT/US2011/059588, filed Nov. 7, 2011, which claims priority to U.S. Provisional Application No. 61/410,672, filed Nov. 5, 2010, each of which is hereby incorporated by reference in its entirety.

The contents of the text file submitted electronically herewith are incorporated herein by reference in their entirety: A computer readable format copy of the Sequence Listing (filename: MIRG_024_01US_SeqList_ST25-2.txt, date recorded: Jul. 22, 2013, file size 29 kilobytes).

FIELD OF THE INVENTION

The present invention relates to modified oligonucleotides with enhanced binding affinity towards complementary polynucleotides.

BACKGROUND

MicroRNAs (miRs) have been implicated in a number of biological processes including regulation and maintenance of cardiac function (Van Rooij et al., "MicroRNAs: Powerful New Regulators of Heart Disease and Proactive Therapeutic Targets," *J. Clin. Invest.* 117(9):2369-2376 (2007); Chien K R, "Molecular Medicine: MicroRNAs and the Tell-tale Heart," *Nature* 447:389-390 (2007)). Therefore, miRs represent a relatively new class of therapeutic targets for conditions such as cardiac hypertrophy, myocardial infarction, heart failure, vascular damage, and pathologic cardiac fibrosis, among others. miRs are small, non-protein coding RNAs of about, 18 to about 25 nucleotides in length, and act as repressors of target mRNAs by promoting their degradation, when their sequences are perfectly complementary, or by inhibiting translation, when their sequences contain mismatches. The mechanism involves incorporation of the mature miRNA strand into the RNA-induced silencing complex (RISC), where it associates with its target RNAs by base-pair complementarity.

miRNA function may be targeted therapeutically by antisense polynucleotides or by polynucleotides that mimic miRNA function ("miRNA mimetic"). However, targeting miRNAs therapeutically with oligonucleotide-based agents poses several challenges, including RNA-binding affinity and specificity, efficiency of cellular uptake, and nuclease resistance. For example, when polynucleotides are introduced into intact cells they are attacked and degraded by nucleases leading to a loss of activity. While polynucleotide analogues have been prepared in an attempt to avoid their degradation, e.g., by means of 2' substitutions (Sproat et al, *Nucleic Acids Research* 17:3373-3386 (1989)), the modifications often affect the polynucleotide's potency for its intended biological action. Such reduced potency, in each case, may be due to an inability of the modified polynucleotide to form a stable duplex with the target RNA and/or a loss of interaction with the cellular machinery. Other modifications include the use of locked nucleic acid, which has the potential to improve RNA-binding affinity (Veedu et al., "Locked Nucleic Acid as a Novel Class of Therapeutic Agent," *RNA Biology* 6:3, 321-323 (2009)).

Oligonucleotide chemistry patterns or motifs for miRNA inhibitors have the potential to improve the delivery, stability, potency, specificity, and/or toxicity profile of the inhibitors, and as such are needed for effectively targeting miRNA function in a therapeutic context.

SUMMARY OF THE INVENTION

The present invention relates to oligonucleotides comprising at least one nucleotide having a 2' modification and at least one nucleotide having an amino carbonyl modified base, as well as pharmaceutical compositions comprising the modified oligonucleotides, and methods of use and synthesis for these oligonucleotides.

In one aspect, the present invention provides oligonucleotides comprising at least one nucleotide having a 2' modification and at least one nucleotide having an amino carbonyl modified base. In various embodiments, the oligonucleotides provide advantages in duplex binding affinity, among other advantages, such as efficiency in RNA knockdown. In some embodiments, the oligonucleotide comprises a nucleotide sequence that is at least substantially complementary to a nucleotide sequence of human miRNA. In other embodiments, the oligonucleotide is at least substantially complementary to a mammalian transcript, other than a miRNA, and is therefore useful for antisense inhibition of gene expression. In still other embodiments, the oligonucleotide comprises the sequence of a human miRNA, and thereby mimics miRNA function. In still other embodiments, the oligonucleotide is a detection probe for in vitro detection or quantification of nucleic acids in a sample, using any conventional platform.

The base modification is an amino carbonyl, such as a carboxamino, carbamoyl, or carbamide group. The modification in various embodiments is at the C-5 position of a pyrimidine base or C-8 of a purine base. The modifying amino carbonyl group of the instant oligonucleotide contains a radical or substituent which can be, without limitation, $C_1$-$C_{18}$ alkyl, $C_1$-$C_{18}$ alkenyl, cycloalkyl, aryl, heteroaryl, heterocyclyl, and —$(CH_2)_n$—$NR_1R_2$, wherein n is an integer from 1 to 6 and $R_1$ and $R_2$ are independently H or $C_1$-$C_6$alkyl. Exemplary moieties include piperidine, piperazine, morpholino, or imidazole, each of which may be substituted or unsubstituted. In other embodiments, the substituent is from C4 to C20 alkyl or alkenyl, phenyl, or an amine.

The oligonucleotide further comprises at least one nucleotide with a 2' modification. In some embodiments, the 2' modifications may be independently selected from C1-6 alkyl, 2' O-alkyl(C1-C6), F, Cl, $NH_2$, CN, or SH. Other potential 2' modifications are described elsewhere herein. An exemplary 2' modification is 2' O-Me, which may provide synergistic enhancements of the oligonucleotide's $T_m$, together with the base modification. In still other embodiments, at least, one nucleotide has a 2' modification that is a 2'-4' bridge locking the sugar in the C3 endo configuration. Unmodified 2' positions may be hydrogen.

The number of nucleotides having a modified base may vary, but in certain embodiments is at least 25% of nucleotides, or at least 50% of nucleotides, or at least 75% of nucleotides or 100% of nucleotides. In some embodiments, the enhancement of $T_m$ may be accomplished with relatively few base-modified nucleotides, such as less than 50% of nucleotides or less than 25% of nucleotides. In some embodiments, the oligonucleotide contains only 1, 2, 3, or 4 base-modified nucleotides. The base modified nucleotides in these embodiments may be pyrimidine bases, such as uridine or thymine, and/or may contain a T modification such as 2' O'Me. That is, the oligonucleotide (e.g., of about 16 nucleotides) may have a single incorporation of a nucleotide having the base modification and 2' OMe modification, with unmodified 2' positions being hydrogen, or alternatively independently selected from LNA.

In certain embodiments, the oligonucleotide further comprises backbone chemistries such as cap modifications and phosphorothioate linkages.

The invention includes the discovery that novel base modified 2'-OMe-pyrimidines show enhancements of duplex binding affinity with their complementary sequences when incorporated into antisense oligonucleotides. Additionally, these pyrimidine base modified 2'-OMe nucleotides with phosphorothioate backbone modifications show biological activity against their microRNA target sequences in cell culture, even without the use of transfection reagents. In vivo activity is also demonstrated herein using a model in vivo system showing knockdown of target miRNA in cardiac tissue.

In another aspect, the present invention provides a method of reducing or inhibiting RNA expression or activity in a cell, a method of preventing or treating a condition in a subject associated with or mediated by RNA or expression thereof, the method using the base modified oligonucleotides described herein.

DESCRIPTION OF THE FIGURES

FIG. 1 is a table showing the amount of $T_m$ enhancement for various base modifications of 2'-OMe-uridine oligonucleotides. Base modifications were carboxamido linkages at C5.

FIG. 5 is a table of experimental $T_m$ measurements for modified anti-miR-208a when duplexed with unmodified miR-208a RNA. All oligonucleotides contain phosphorothioate linkages; +U stands for base modified nucleotide with 2' OMe; m stands for 2' OMe, +U stands for C18 base modification and 2' OMe ribose; l stands for LNA modification; d stands for DNA.

DETAILED DESCRIPTION OF THE INVENTION

Figure 2:
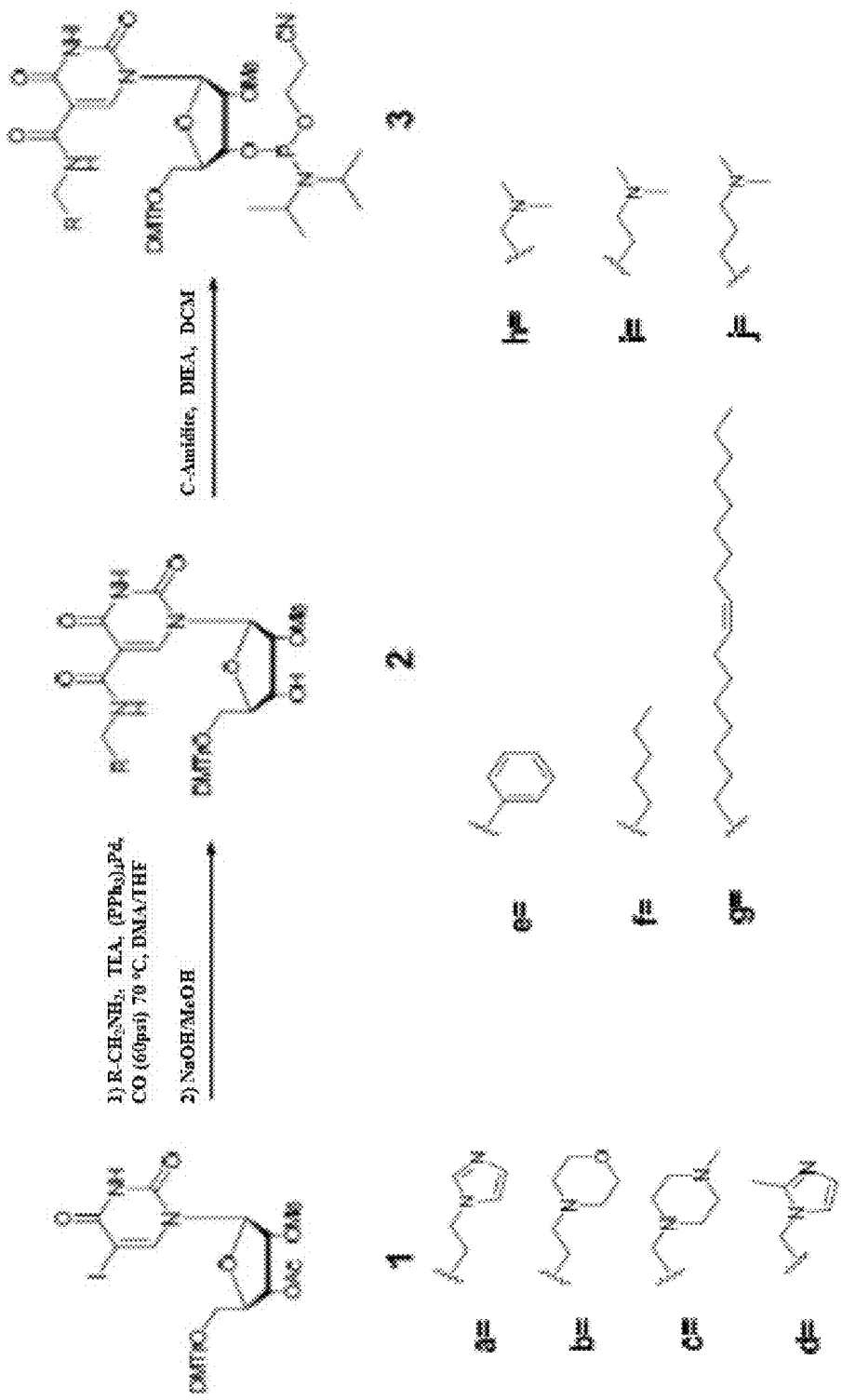
FIG. 2 illustrates the synthesis of modified monomeric nucleosides and corresponding phosphoramidites for incorporation into oligonucleotides.

The present invention relates to oligonucleotides comprising at least one nucleotide having a 2' modification and at least one nucleotide having an amino carbonyl modified base. The present invention further relates to methods of use and synthesis for these oligonucleotides.

Studies of nucleoside base modification have been largely limited to investigations of effects on gene expression. Certain nucleobase derivatives, especially C-5 propynylated pyrimidines, have exhibited only modest gains in affinity/duplex stability for DNA/RNA duplexes (Znosko et al, *J. Am. Chem. Soc.*, 125(20):6090-6097 2003)). More complex pendant functional groups (except as to known intercalators), are considered less likely to increase oligonucleotide affinity, given the potential competing effects of hydrophobicity or steric effects (Hashimoto et al., J. Am. Chem. Soc., 115(16): 7128-7134 (1993)). Similarly to sugar alterations, base modification may potentially change the overall hydrophobicity and hydrogen bonding characteristic of an oligonucleotide bearing the modification, and might even lead to non-canonical base pairing interactions (Vaught et al., *J. Am. Chem. Soc.*, 132(12):4141-4151 (2010)), an effect that is not desirable for sequence-specific RNA inhibition.

In one aspect, the present invention provides oligonucleotides comprising at least one nucleotide having a 2' modification and at least one nucleotide having an amino carbonyl modified base. In various embodiments, the oligonucleotides provide advantages in duplex binding affinity, among other advantages, such as efficiency in RNA knockdown.

In some embodiments, the oligonucleotide comprises a nucleotide sequence that is at least substantially complementary to a nucleotide sequence of human miRNA. In other embodiments, the oligonucleotide is substantially complementary or fully complementary to a mammalian transcript, other than a miRNA, and is therefore useful for antisense inhibition of gene expression. In still other embodiments, the oligonucleotide comprises a sequence of a human miRNA sufficient to mimic of miRNA function. In other embodiments, the oligonucleotide is a detection probe for in vitro detection or quantification of nucleic acids in a sample, using any conventional platform, such as a microarray or other hybridization-based platform.

In some embodiments, the oligonucleotide is from about 6 to about 22 nucleotides in length. The oligonucleotides having one or more of the base, sugar, and/or backbone modifications disclosed herein can be, for example, from 8 to 18 nucleotides in length, or from 12 to 16 nucleotides in length. In certain embodiments, the oligonucleotide is about 8 nucleotides in length, about 9 nucleotides in length, about 10 nucleotides in length, about 11 nucleotides in length, about 12 nucleotides in length, about 13 nucleotides in length, about 14 nucleotides in length, about 15 nucleotides in length, or about 16 nucleotides in length. For example, where the oligonucleotide targets miR-208a, the oligonucleotide may have the sequence CTTTTTGCTCGTCTTA (SEQ ID NO:64).

The base modification is generally an amino carbonyl, such as a carboxamino, carbamoyl, or carbamide group. The modification in various embodiments is at the C-5 position of one or more pyrimidine bases, and/or at C-8 of one or more purine bases. The modifying amino carbonyl group of the instant oligonucleotide contains a radical or substituent which can be, without limitation, $C_1$-$C_{18}$ alkyl, $C_1$-$C_{18}$ alkenyl, cycloalkyl, aryl, heteroaryl, heterocyclyl, and —$(CH_2)_n$—$NR_1R_2$, wherein n is an integer from 1 to 6 and $R_1$ and $R_2$ are independently H or $C_1$-$C_6$alkyl.

Figure 6:
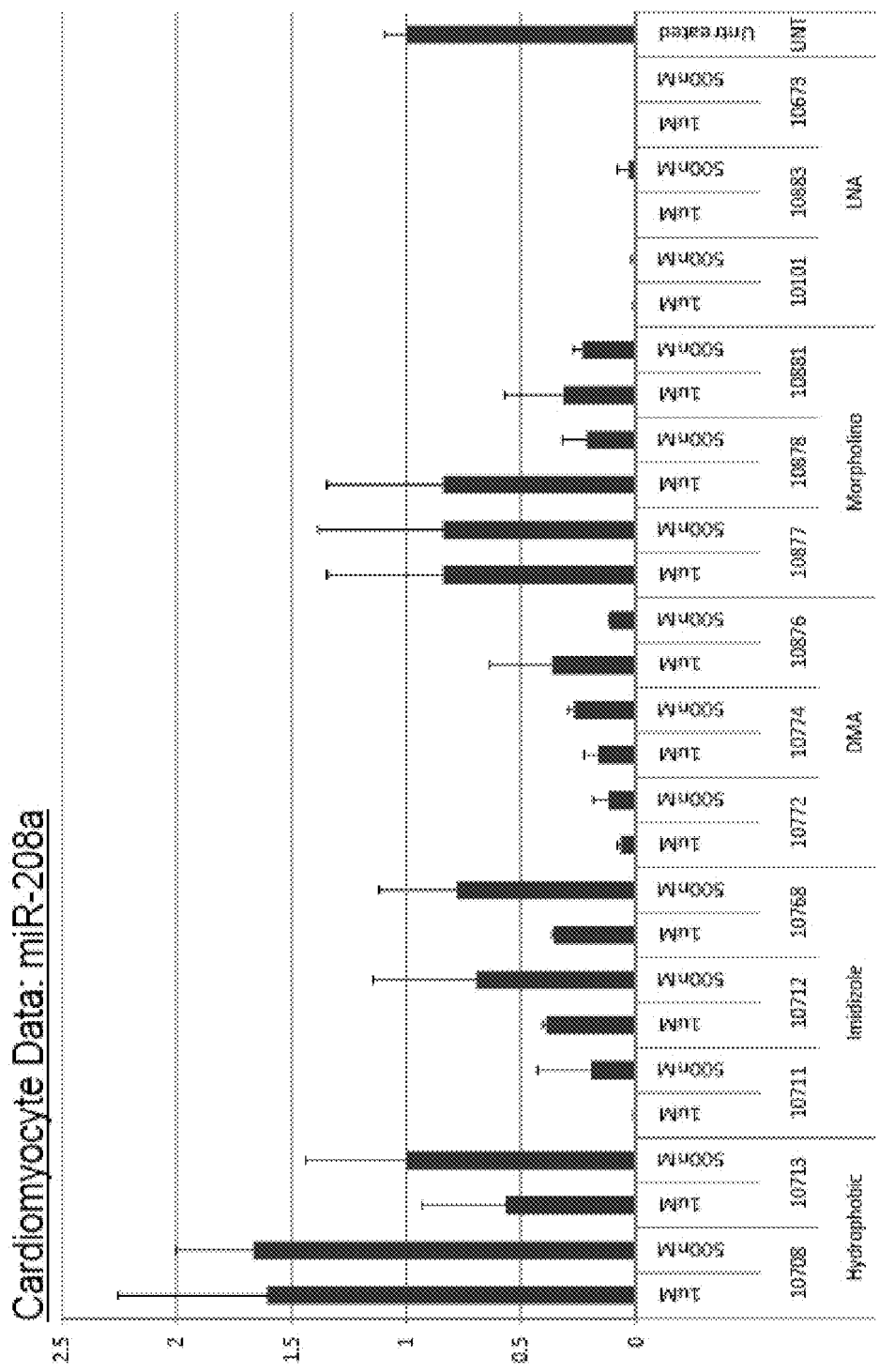
FIG. 6 shows a miR-208a knockdown by modified anti-miR-208a in rat primary neonatal cardiomyocytes without lipid transfection reagent.

For example, in some embodiments, the radical or substituent, is a nitrogen-containing heterocycle, such as, for example, piperidine, piperazine, morpholino, or imidazole, each of which may be substituted or unsubstituted with one, two, or three alkyl or alkenyl substituents (e.g., C1-8 or C1-4). Examples include 2-ethyl, 1-methyl-imidazole, 3-propyl imidazole, and propyl morpholino, which are depicted in FIG. 1. In other embodiments, the radical or substituent is a carbocyclic group, such as a cycloalkyl (e.g., C5 to C8) or phenyl, which may optionally be substituted with one or more (e.g., 1, 2, or 3) alkyl or alkenyl substituents (e.g., C1-8 or C1-4). Examples include Benzyl as shown in FIG. 6. In still other embodiments, the radical or substituent is a secondary or tertiary amine, for example, having one or two alkyl or alkenyl substituents (e.g., C1-8, or C1-4). Examples include propyl dimethyl amino, and ethyl dimethyl amino, as shown in FIG. 1. In some embodiments, the modifying amino carbonyl group contains a lipophilic or hydrophilic substituent, and in some embodiments, the substituent is cationic. Examples include C6 and C18 alkyl as shown in FIG. 1. In some embodiments, the radical or substituent is bound to the C5 position of a pyrimidine base through a carboxamino linkage, optionally having a linking group of from 1 to 4 carbon units. The radical or substituent may be as described elsewhere herein.

In some embodiments, the base modification contains a group that is positively charged, and optionally having multiple positive charges, under physiological conditions, such as a pipirazine. Primary, secondary and quaternary amines can also be used as suitable base modifications. In various embodiments, the base modification contains a peptide linkage, which are more likely to be metabolized into less toxic nucleobases.

In some embodiments, the base modified nucleotides are incorporated in the middle of the sequence. For example, in some embodiments, the modified nucleotides are not incorporated at the last 1, 2, or 3 nucleotides on the 5' and 3' ends. Moieties that are cationic under physiological conditions can provide substantial increases in $T_m$. Notably, imidazole and morpholine derivatives that have pKa's in the range of 6.5-7.5 provide substantial binding and biological activity. Trialkylamines are also shown herein to be effective. Other cationic species of interest include guanidine type derivatives and hydrazines or hydroxylamines. Also of note are substituted piperazines, moieties that often act pharmacologically similar to morpholines due to similar pKa's, but that have two cationic centers. Hydrophobic substitutions such as benzyl and alkyl moieties may also enhance $T_m$, provide nuclease resistance, and/or aid in cytosolic delivery.

In accordance with the present invention, the biological activity and $T_m$ enhancement may be due in-part to an increase in enthalpic binding, and therefore, the modified oligonucleotides have the potential to enhance mismatch discrimination, and are thus useful as probes for diagnostic applications.

The oligonucleotide further comprises at least one nucleotide with a 2' modification. As used herein, the term "2' modification" includes any 2' group other than H or OH. For example, the 2' modifications may be independently selected from C1-6 alkyl, 2'O-alkyl(C1-C6), F, Cl, NH$_2$, CN, or SH. Other potential 2' modifications are described elsewhere herein. An exemplary 2' modification is 2' O-Me, which may provide synergistic enhancements of the oligonucleotide's $T_m$, together with the base modification (e.g., when incorporated in the same nucleotide). In still other embodiments, at least one nucleotide has a 2' modification that is a 2'-4' bridge locking the sugar in the C3 endo configuration.

In these or other embodiments, the oligonucleotide contains a 2' modification selected from alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl, or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Other exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

The oligonucleotide may have several nucleotides with the base modification as described, such as from 1 to about 10, or about 2 to about 9 nucleotides. In some embodiments, the oligonucleotide contains (exactly) 1, 2 or 3 nucleotides having the modified base. The oligonucleotide may also, independently, have several nucleotides modified at the 2' position. That is, the base modified nucleotides may also contain a 2' modification as described, such as a 2'OMe modification. In some embodiments, at least one or two nucleotides have both a modified base and modified 2' position, each as described above. In certain embodiments, the oligonucleotide comprises a nucleotide with a base modification shown in FIG. 1, together with a 2'OMe modification. The oligonucleotide in certain embodiments has exactly one, two, or three of such modified nucleotides.

Where the 2' modification is a 2'-4' bridge, the 2' modification may be locked nucleic acid (LNA). LNAs are described, for example, in U.S. Provisional Application Ser. No. 61/495,224, U.S. Pat. No. 6,268,490, U.S. Pat. No. 6,316,198, U.S. Pat. No. 6,403,566, U.S. Pat. No. 6,770,748, U.S. Pat. No. 6,998,484, U.S. Pat. No. 6,670,461, and U.S. Pat. No. 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

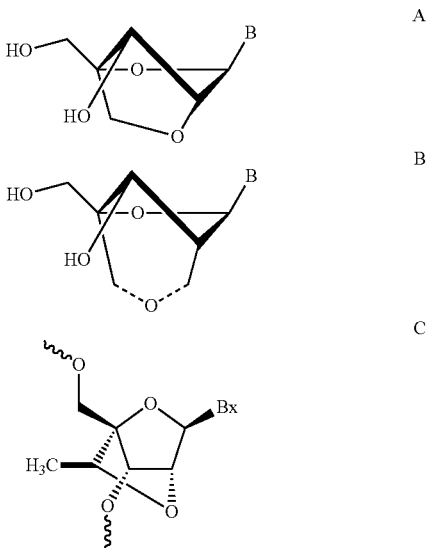

Other suitable locked nucleotides that can be incorporated in the oligonucleotides of the invention include those described in U.S. Pat. No. 6,403,566 and U.S. Pat. No. 6,833,361, both of which are hereby incorporated by reference in their entireties.

The oligonucleotide may contain at, least 3, at least 5, or at least 7 locked nucleotides, and in various embodiments is not fully comprised of locked nucleotides. In some embodiments, the number and position of locked nucleotides may be as described in No. 61/495,224, which is hereby incorporated by reference, and particularly for miR-208 family inhibitors.

The oligonucleotide may have one or more 2'-deoxy nucleotides, and in some embodiments, contains from 2 to about 10 2'-deoxy nucleotides, in some embodiments, at least one, or all, base-modified nucleotides are 2' deoxy.

The number of nucleotides having a modified base may vary, but in certain embodiments is at least 25% of nucleotides, or at least 50% of nucleotides, or at least 75% of nucleotides, or 100% of nucleotides. As shown herein, the enhancement of $T_m$ may be accomplished with relatively few base-modified nucleotides, such as less than 50% of nucleotides or less than 25% of nucleotides in some embodiments. However, in some embodiment, the oligonucleotide contains only 1, 2, 3, or 4 base-modified nucleotides (e.g., as shown in FIG. 1), and such base-modified nucleotides may also contain a 2' modification such as 2' OMe. The base modified nucleotides in these embodiments may be pyrimidine bases, such as uridine or thymine in some embodiments. In some embodiments, the oligonucleotide contains a single incorporation of a base-modified oligonucleotide having a 2' OMe.

In some embodiments, the oligonucleotide contains at least 6, or at least 9 nucleotides having a 2'-OMe. Alternatively, all nucleotides (or all purines or all pyrimidines in some embodiments) may be 2' O-Me.

The cationic class of C-5 modified bases exhibited substantial $T_m$ enhancement (as shown herein), in addition to some lipophilic enhancements to the C-5 position of 2'-OMe-Uridine. Beyond simple Watson-Crick base pairing to miRNA's of interest, mixtures of modifications containing both lipophilic and cationic moieties may have a larger effect on miRNA's already associated with intracellular enzymes and proteins that regulate the miRNA's activity. These chimeric nucleotides may not only associate with their complementary target sequence, but also interact with hydrophobic or hydrophilic regions of the protein associated with the miRNA.

In certain embodiments, the oligonucleotide further comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure as described herein may increase resistance of the oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at, least one terminal phosphorothioate monophosphate. The phosphorothioate monophosphate may be at the 5' and/or 3' end of the oligonucleotide. A phosphorothioate monophosphate is defined by the following structures, where B is base, and R is a 2' modification as described above:

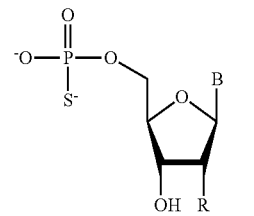

5' phosphorothioate monophosphate

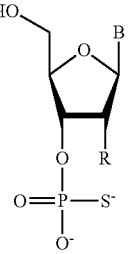

3' phosphorothioate monophosphate

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

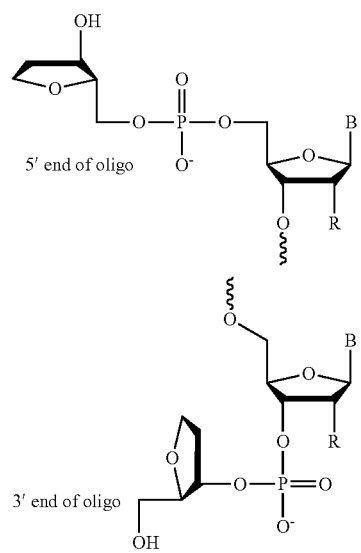

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phophodiester linkages. In certain embodiments, however, the oligonucleotide is fully phosphorothioate-linked. In other embodiments, the oligonucleotide has from one to five or one to three phosphate linkages.

The synthesis of oligonucleotides, including modified polynucleotides, by solid phase synthesis is well known and is reviewed by Caruthers et al., "New Chemical Methods for Synthesizing Polynucleotides," *Nucleic Acids Symp. Ser.*, (7):215-23 (1980) which is hereby incorporated by reference in its entirety.

Figure 8:
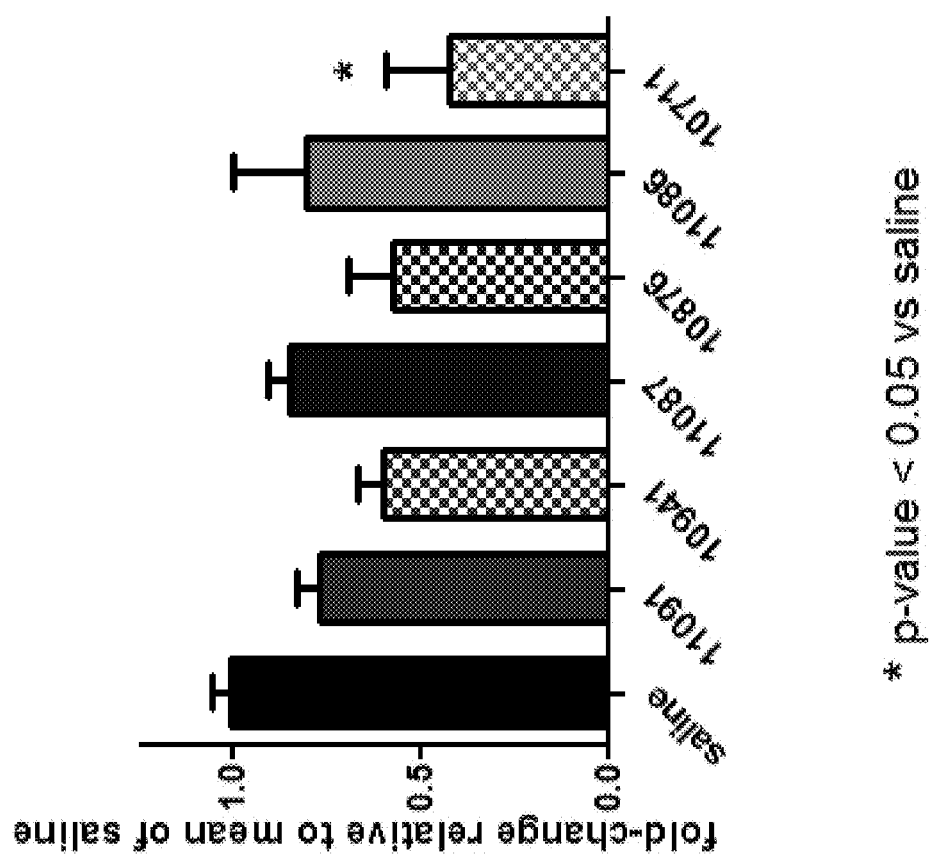
FIG. 8 is a plot of in vivo efficacy of base modified oligonucleotides in C57BL/6 mice. The plot shows the fold-change relative to saline injections for some modified oligonucleotides.

The invention includes the discovery that novel base modified 2'-OMe-pyrimidines show enhancements of duplex binding affinity with their complementary sequences when incorporated into 2'-OMe nucleotides (See FIG. 1). Additionally, these pyrrolidine base modified 2'-OMe nucleotides with phosphorothioate backbone modifications show biological activity against their microRNA target, sequences in cell culture, even without the use of transfection reagents, a characteristic that unconjugated 2'-OMe phosphorothioate nucleotides do not exhibit without the use of special 3' and 5'-conjugates. Further, as shown herein, pyrimidine base modified 2'-OMe nucleotides with phosphorothioate backbone modifications exhibit knockdown of target miRNA in cardiac tissue following saline injection (FIG. 8).

Figure 3:
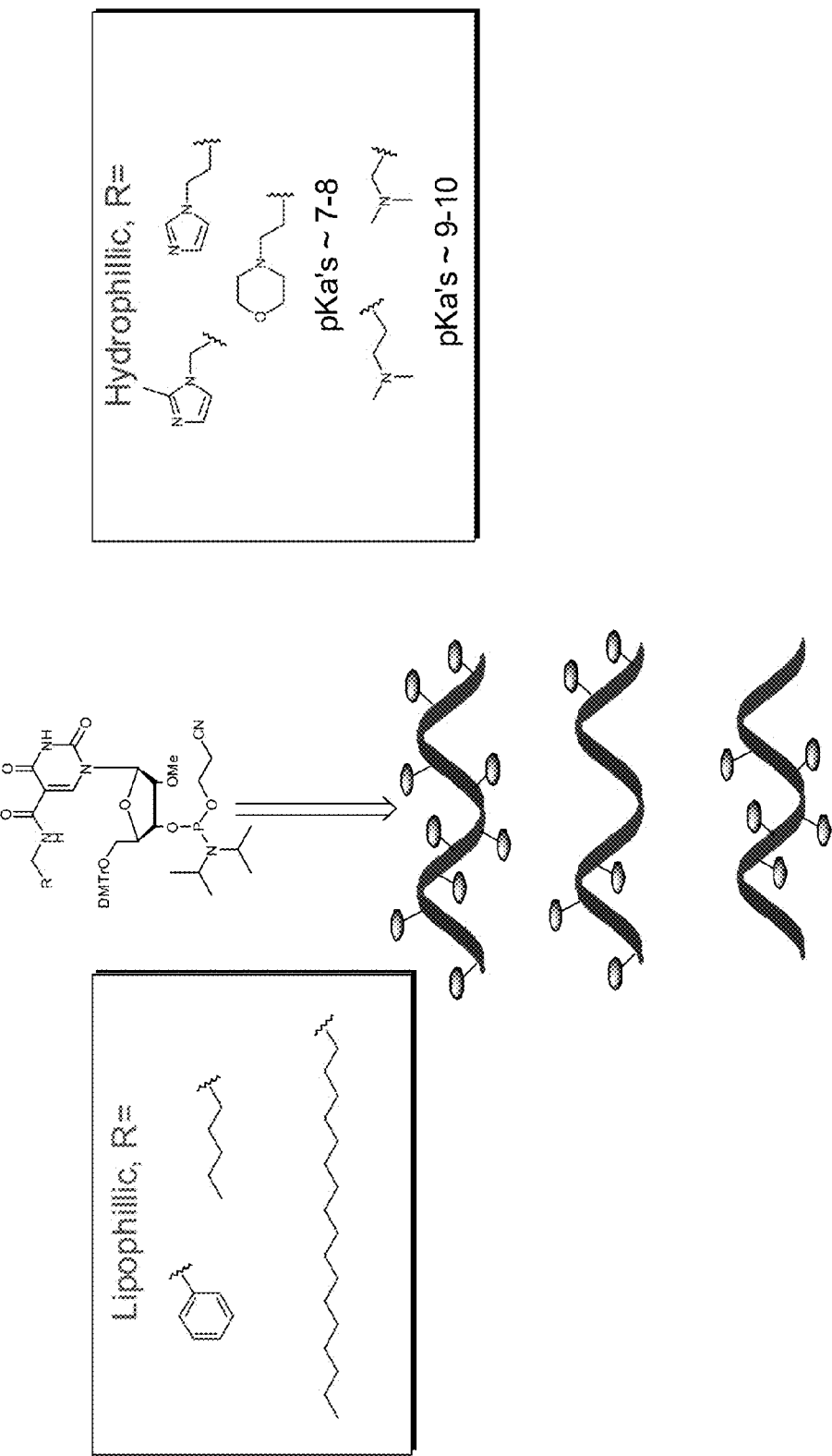
FIG. 3 illustrates hydrophilic and hydrophobic nucleoside modifications synthesized via the scheme in FIG. 2 and shows some example incorporation patterns in oligonucleotides.
Figure 4:
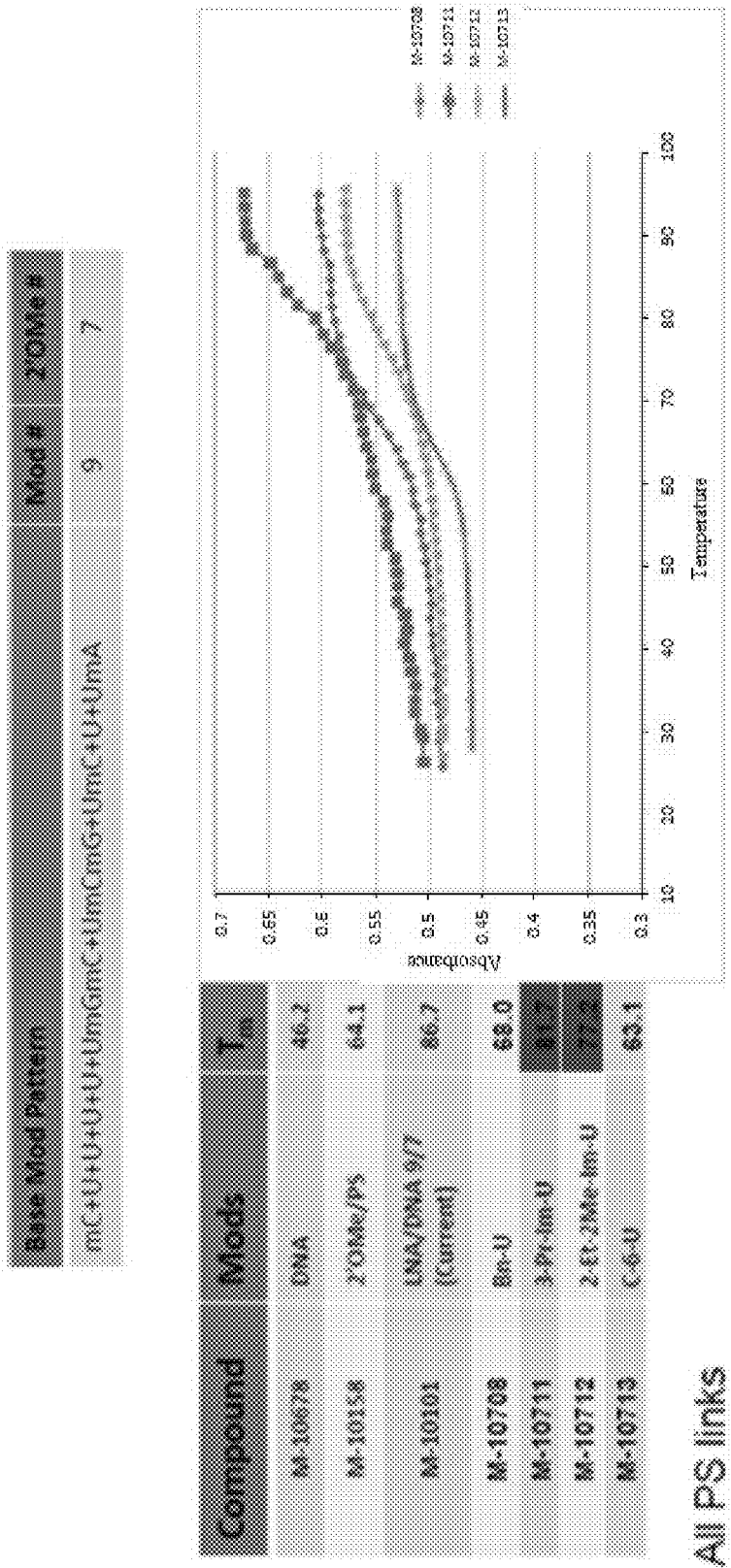
FIG. 4 compares $T_m$ measurements for several base modifications against LNA/DNA, 2'-OMe phosphorothioate, and DNA oligonucleotide. The base modification pattern is shown.
Figure 7:
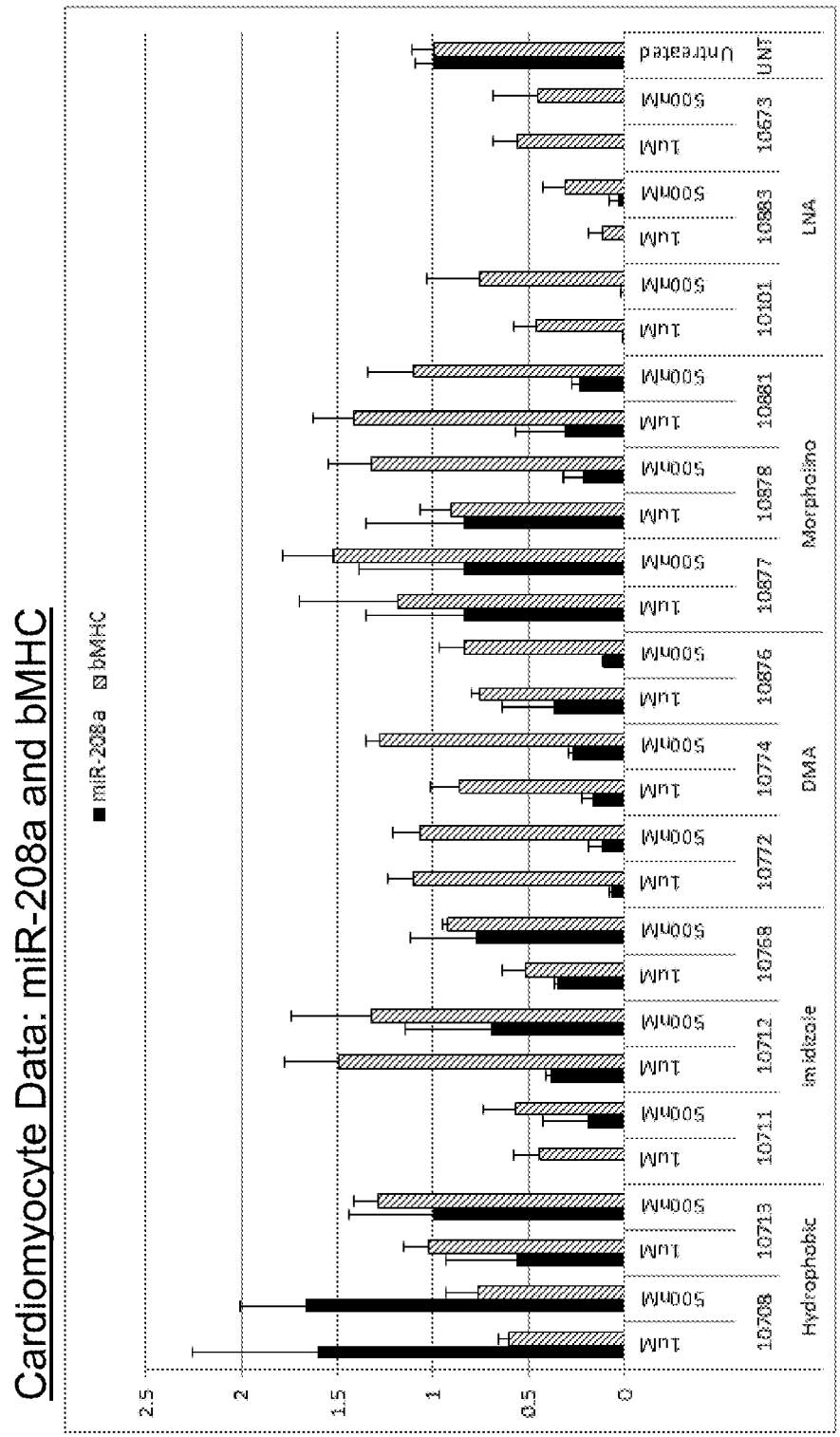
FIG. 7 shows the miR-208a knockdown data in FIG. 6 superimposed on bMHC levels.

A series of model compounds were synthesized where the pendant modification on the C-5 base position were either hydrophobic or hydrophilic. Structures are included in FIGS. 1-3. Anti-miRNA oligonucleotides containing only C-5 hydrophobic modifications of all of the 2'-OMe-uridine nucleosides, modestly increases the $T_m$ of a duplex compared to the nucleotides with unmodified 2'-OMe-uridine. These nucleotides did not provide substantial benefit with respect to miRNA inhibition in cell culture experiments, both with and without lipid transfection reagents (FIGS. 6 and 7). In contrast, anti-miRNA nucleotides containing hydrophilic, amine (cationic) containing pendant, groups alone on C-5 of all uridines showed large increases in $T_m$ (FIGS. 4-6). Furthermore, cell culture experiments with nucleotides containing these modifications show unique biological properties such as the ability to inhibit, miRNA targets, even in the absence of lipid transfection reagents or conjugates. It should also be noted that some nucleotides with combinations of hydrophobic and cationic base modifications showed good anti-miRNA activity.

Without being bound by theory, it is believed that these pyrimidine base modifications enhance binding affinity through interaction with the polar major groove of the resulting RNA duplexes. The nucleosides described herein are modified, for example, via carboxamido modifications that are cross conjugated to the pyrimidine base and provide additional hydrogen bonding sites, either to another nucleobase or to the polar major groove. This is a distinct mode of duplex stabilization than commonly used sugar modifications, such as bridged nucleosides and 2'-modifications, that favor A-form conformations of the nucleobase which enhance binding to RNA. Therefore, it is believed that these C-5 carboxamido-modified nucleobases will act at least additively to the binding enhancement provided by sugar modification. C-5 carboxamido-modified nucleosides that also contain a 2'-4'-bridged sugar can also be employed to achieve enhanced binding of the oligonucleotides to their target, including the bridge structure shown below. Oligonucleotides incorporating the 2'-CBBN nucleosides are described in U.S. Provisional Application No. 61/532,738, which is hereby incorporated by reference. As shown in the structure below, R represents the carboxamido modification described herein, and R' and R" represent the 5' and 3' ends.

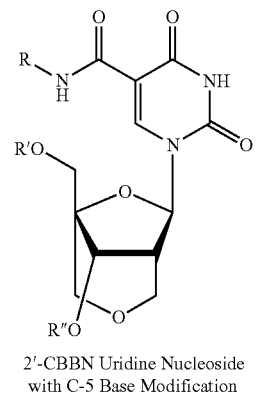

2'-CBBN Uridine Nucleoside
with C-5 Base Modification

The carboxamido-modifications of the C-5 position of uridine, and the chemistry and stabilization characteristics, can be extended to the cytidine base. Similar modifications can be employed for purine bases via carboxamido-type modifications described herein.

Nucleotides incorporating the modified nucleobases described herein display enhanced binding affinity to their complementary nucleotides. Increases in $T_m$ have been measured as high as 5° C./incorporation (FIG. 5), comparable to the bicyclic LNA monomers that, to this point, have been observed to be the most effective and widely used affinity enhancing modification. The enhancement of $T_m$ may be especially effective in creating more active and potent microRNA inhibitors. Additionally, some of these new nucleobase modifications likely enhance cellular uptake by either masking some of the negatively charged phosphates, in the case of cationic moieties, or, in the case of lipophilic modifications, by shielding the backbone from nucleases and creating an amphiphillic nucleotide (FIGS. 6, 7, and 8).

The modifications may be used in oligonucleotides designed to mimic miRNA sequences, and may comprise any one of the mature miRNA sequences in Table 1 below. Such antisense and sense sequences may be incorporated into shRNAs or other RNA structures containing stem and loop portions, for example. Such sequences are useful for, among other things, mimicking or targeting miRNA function for treatment or ameliorating cardiac hypertrophy, myocardial infarction, heart failure (e.g., congestive heart failure), vascular damage, and/or pathologic cardiac fibrosis, among others. Exemplary miRNA therapeutic utilities are disclosed in the US and PCT patent references listed in Table 1 below, each of which is hereby incorporated by reference in its entirety. The mature and pre-processed forms of miRNAs are disclosed in the patent references listed below, and such descriptions are also hereby incorporated by reference.

TABLE 1

| miRNA | miRNA Sequence | Reference |
|---|---|---|
| 1 | UGGAAUGUAAAGAAGUAUGUAU (SEQ ID No. 1) | WO 2009/012468 |
| 100 | AACCCGUAGAUCCGAACUUGUG (SEQ ID No. 2) | WO 2009/012468 |
| 10b | UACCUGUAGAACCGAAUUUGUG (SEQ ID No. 3) | WO 2009/012468 |
| 125b | UCCCUGAGACCCUAACUUGUGA (SEQ ID No. 4) | WO 2009/012468 |
| 128 | UCACAGUGAACCGGUCUCUUU (SEQ ID No. 5) | WO 2007/070483 |
| 133a | UUUGGUCCCCUUCAACCAGCUG (SEQ ID No. 6) | WO 2009/012468 |
| 133b | UUUGGUCCCCUUCAACCAGCUA (SEQ ID No. 7) | WO 2009/012468 |
| 139 | UCUACAGUGCACGUGUCUCCAG (SEQ ID No. 8) | WO 2009/012468 |
| 143 | UGAGAUGAAGCACUGUAGCUC (SEQ ID No. 9) | WO 2007/070483 |
| 145 | GUCCAGUUUUCCCAGGAAUCCCU (SEQ ID No. 10) | WO 2007/070483 |
| 150 | UCUCCCAACCCUUGUACCAGUG (SEQ ID No. 11) | WO 2009/012468 |
| 15a | UAGCAGCACAUAAUGGUUUGUG (SEQ ID No. 12) | WO 2009/062169 |
| 15b | UAGCAGCACAUCAUGGUUUACA (SEQ ID No. 13) | WO 2009/062169 |
| 16 | UAGCAGCACGUAAAUAUUGGCG (SEQ ID No. 14) | WO 2009/062169 |
| 181b | AACAUUCAUUGCUGUCGGUGGGU (SEQ ID No. 15) | WO 2009/012468 |
| 195 | UAGCAGCACAGAAAUAUUGGC (SEQ ID No. 16) | WO 2009/012468 |
| 197 | UUCACCACCUUCUCCACCCAGC (SEQ ID No. 17) | WO 2009/012468 |
| 199a | CCCAGUGUUCAGACUACCUGUUC (SEQ ID No. 18) | WO 2009/012468 |
| 199B | miR-199b-5p CCCAGUGUUUAGACUAUCUGUUC (SEQ ID No. 19) miR-199b-3p ACAGUAGUCUGCACAUUGGUUA (SEQ ID No. 20) | US 61/047,005 |
| 206 | UGGAAUGUAAGGAAGUGUGUGG (SEQ ID No. 21) | WO 2007/070483 |
| 208a | AUAAGACGAGCAAAAAGCUUGU (SEQ ID No. 22) | WO 2008/016924 |
| 208b | AUAAGACGAACAAAAGGUUUGU (SEQ ID No. 23) | WO 2009/018492 |
| 20a | UAAAGUGCUUAUAGUGCAGGUAG (SEQ ID No. 24) | US 60/950,565 |
| 21 | UAGCUUAUCAGACUGAUGUUGA (SEQ ID No. 25) | WO 2009/058818 |
| 214 | ACAGCAGGCACAGACAGGCAGU (SEQ ID No. 26) | US 61/047,005 |
| 22 | AAGCUGCCAGUUGAAGAACUGU (SEQ ID No 27) | WO 2009/012468 |
| 221 | AGCUACAUUGUCUGCUGGGUUUC (SEQ ID No. 28) | WO 2009/012468 |
| 222 | AGCUACAUCUGGCUACUGGGU (SEQ ID No. 29) | WO 2009/012468 |
| 224 | CAAGUCACUAGUGGUUCCGUU (SEQ ID No. 30) | WO 2009/012468 |
| 23a | AUCACAUUGCCAGGGAUUUCC (SEQ ID No. 31) | WO 2009/012468 |
| 26a | UUCAAGUAAUCCAGGAUAGGCU (SEQ ID No. 32) | WO 2007/070483 |
| 26b | UUCAAGUAAUUCAGGAUAGGU (SEQ ID No. 33) | WO 2009/012468 |
| 28 | AAGGAGCUCACAGUCUAUUGAG (SEQ ID No. 34) | WO 2009/012468 |
| 29a | UAGCACCAUCUGAAAUCGGUUA (SEQ ID No. 35) | WO 2009/018493 |
| 29b | UAGCACCAUUUGAAAUCAGUGUU (SEQ ID No. 36) | WO 2009/018493 |
| 29c | UAGCACCAUUUGAAAUCGGUUA (SEQ ID No. 37) | WO 2009/018493 |
| 30a | UGUAAACAUCCUCGACUGGAAG (SEQ ID No. 38) | PCT/US2010/031147 |

TABLE 1-continued

| miRNA | miRNA Sequence | Reference |
|---|---|---|
| 30b | UGUAAACAUCCUACACUCAGCU (SEQ ID No. 39) | PCT/US2010/031147 |
| 30c | UGUAAACAUCCUACACUCUCAGC (SEQ ID No. 40) | WO 2009/012468 |
| 30d | UGUAAACAUCCCCGACUGGAAG (SEQ ID No. 41) | PCT/US2010/031147 |
| 30e | UGUAAACAUCCUUGACUGGAAG (SEQ ID No. 42) | PCT/US2010/031147 |
| 342-3p | UCUCACACAGAAAUCGCACCCGU (SEQ ID No. 43) | WO 2009/012468 |
| 382 | GAAGUUGUUCGUGGUGGAUUCG (SEQ ID No. 44) | WO 2009/012468 |
| 422a | ACUGGACUUAGGGUCAGAAGGC (SEQ ID No. 45) | US 2009/0226375 |
| 378 | ACUGGACUUGGAGUCAGAAGG (SEQ ID No. 46) | WO 2009/012468 |
| 424 | CAGCAGCAAUUCAUGUUUUGAA (SEQ ID No. 47) | WO 2009/062169 |
| 483-3p | UCACUCCUCUCCUCCCGUCUU (SEQ ID No. 48) | WO 2009/012468 |
| 484 | UCAGGCUCAGUCCCCUCCCGAU (SEQ ID No. 49) | WO 2009/012468 |
| 486-5p | UCCUGUACUGAGCUGCCCCGAG (SEQ ID No. 50) | WO 2009/012468 |
| 497 | CAGCAGCACACUGUGGUUUGU (SEQ ID No. 51) | WO 2009/062169 |
| 499 | UUAAGACUUGCAGUGAUGUUU (SEQ ID No. 52) | WO 2009/018492 |
| 542-5p | UCGGGGAUCAUCAUCACGAGA (SEQ ID No. 53) | WO 2009/012468 |
| 92a | UAUUGCACUUGUCCCGGCCUGU (SEQ ID No. 54) | WO 2009/012468 |
| 92b | UAUUGCACUCGUCCCGGCCUCC (SEQ ID No. 55) | WO 2009/012468 |
| let-7a | UGAGGUAGUAGGUUGUAUAGUU (SEQ ID No. 56) | WO 2009/012468 |
| let-7b | UGAGGUAGUAGGUUGUGUGGUU (SEQ ID No. 57) | WO 2009/012468 |
| let-7c | UGAGGUAGUAGGUUGUAUGGUU (SEQ ID No. 58) | WO 2009/012468 |
| let-7d | AGAGGUAGUAGGUUGCAUAGUU (SEQ ID No. 59) | WO 2009/012468 |
| let-7e | UGAGGUAGGAGGUUGUAUAGUU (SEQ ID No. 60) | WO 2009/012468 |
| let-7f | UGAGGUAGUAGAUUGUAUAGUU (SEQ ID No. 61) | WO 2009/012468 |
| let-7g | UGAGGUAGUAGUUUGUACAGUU (SEQ ID No. 62) | WO 2009/012468 |
| 451 | AAACCGUUACCAUUACUGAGUU (SEQ ID No. 63) | PCT/US2010/034227 |

In some embodiments, the oligonucleotide targets a miR-208 family miRNA, such as miR-208a or miR-208b, or alternatively miR-15b or miR-21. In some embodiments, the oligonucleotide has a sequence and structure shown in FIG. 5. "m" refers to 2' OMe modification, and "+" refers to base-modified nucleotide with 2' OMe. Descriptions of abbreviations are found in FIG. 1 and FIG. 5.

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

In another aspect, the present invention relates to a pharmaceutical composition which comprises an effective amount of the oligonucleotide of the present invention or a its pharmaceutically-acceptable, and a pharmaceutically-acceptable carrier or diluent.

The composition or formulation may employ a plurality of therapeutic oligonucleotides, including at least one described herein. For example, the composition or formulation may employ at least 2, 3, 4, or 5 miRNA inhibitors described herein.

The oligonucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macro-molecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are hereby incorporated by reference in their entireties.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor oligonucleotide (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). The stability and/or potency of the oligonucleotides disclosed herein allows for convenient routes of administration, including subcutaneous, intradermal, and intramuscular. Pharmaceutical compositions comprising miRNA inhibitors may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredients) plus any additional desired ingredient from, a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologies standards.

In another aspect, the present invention provides a method of reducing or inhibiting RNA expression or activity in a cell. In such embodiments, the method comprises contacting the cell with a modified oligonucleotide (or pharmaceutical composition thereof) having a chemistry pattern described herein, where the oligonucleotide hybridizes (e.g., is at least substantially complementary to) an RNA transcript expressed by the cell. In some embodiments, the RNA is a miRNA.

In another aspect, the present invention provides a method of preventing or treating a condition in a subject associated with or mediated by RNA or expression thereof. In some embodiments, the RNA is a miRNA. The method of prevention or treatment according to the present invention involves administering to the subject a pharmaceutical composition which comprises an effective amount of the base-modified oligonucleotide or a its pharmaceutically-acceptable composition thereof.

The invention provides a method for delivering the modified oligonucleotides to a mammalian cell (e.g., as part of a composition or formulation described herein), and methods for treating, ameliorating, or preventing the progression of a condition in a mammalian patient. The oligonucleotide or pharmaceutical composition may be contacted in vitro or in vivo with a target cell (e.g., a mammalian cell). The cell may be a heart cell.

The method generally comprises administering the oligonucleotide or composition comprising the same to a mammalian patient or population of target cells. The oligonucleotide, as already described, may be a miRNA inhibitor (e.g., having a nucleotide sequence designed to inhibit expression or activity of a miRNA). For example, where the miRNA inhibitor is an inhibitor of a miR-208 family miRNA, the patient may have a condition associated with, mediated by, or resulting from, miR-208 family expression. Such conditions include, for example, cardiac hypertrophy, myocardial infarction, heart failure (e.g., congestive heart failure), vascular damage, restenosis, or pathologic cardiac fibrosis, cancer, or other miRNA associated disorder, including those disorders described in the patent publication listed in Table 1. Thus, the invention provides a use of the modified oligonucleotides and compositions of the invention for treating such conditions, and for the preparation of medicaments for such treatments.

In certain embodiments, the patient (e.g., human patient) has one or more risk factors including, for example, long standing uncontrolled hypertension, uncorrected valvular disease, chronic angina, recent myocardial infarction, congestive heart failure, congenital predisposition to heart disease and pathological hypertrophy. Alternatively or in addition, the patient may have been diagnosed as having a genetic predisposition to, for example, cardiac hypertrophy, or may have a familial history of, for example, cardiac hyper trophy.

In this aspect, the present invention may provide for an improved exercise tolerance, reduced hospitalization, better quality of life, decreased morbidity, and/or decreased mortality in a patient with heart failure or cardiac hypertrophy.

In certain embodiments, the activity of micoRNA in cardiac tissue, or as determined in patient serum, is reduced or inhibited.

In various embodiments, the pharmaceutical composition is administered by parenteral administration or by direct injection into heart tissue. The parenteral administration may be intravenous, subcutaneous, or intramuscular. In some embodiments, the composition is administered by oral, transdermal, sustained release, controlled release, delayed release, suppository, catheter, or sublingual administration. In certain embodiments, the oligonucleotide is administered at, a dose of 25 mg/kg or less, or a dose of 10 mg/kg or less, or a dose of 5 mg/kg or less. In these embodiments, the oligonucleotide or composition may be administered by intramuscular or subcutaneous injection, or intravenously.

In some embodiments, the methods further comprise scavenging or clearing the miRNA inhibitors following treatment. For example, a oligonucleotide having a nucleotide sequence that is complementary to the inhibitor may be administered after therapy to attenuate or stop the function of the inhibitor.

All references cited herein, including those in Table 1, are hereby incorporated by reference for all purposes.

EXAMPLES

Example 1

General Procedure For Preparation of 5-position-modified 2'-O-methyluridine nucleoside phosphoramidites 5-Iodo-2'-O-methyluridine was readily synthesized by known methods, and is also commercially available. The 5'- and 3'-hydroxy 1 groups of the nucleoside are protected by standard 4,4'-Dimethoxytritylation and acetylation methods, respectively. This doubly protected nucleoside was then subjected to carboxamidation by dissolving the nucleoside in a 1:1 mixture of anhydrous THF and N,N-dimethylacetamide in a 50 mL borosilicate boston round bottle. 5 equivalents of TEA and 3 equivalents of a primary amine or amine hydrochloride were added to the mixture followed by addition of 0.1 equiv. of tetrakis(triphenylphosphine)palladium(0). The bottle was placed in a 300 mL Parr Bomb fitted with a scalable inlet and pressure gauge. The apparatus was flushed with carbon monoxide by charging to 60 psi with carbon monoxide then releasing the pressure to 10 psi and repeating twice. The apparatus was then charged to 60 psi, sealed and placed in a 70° C. oil bath for 17 h. The solvent was removed in vacuo, the residue re-dissolved in MeOH and de-acetylated at 55° C. under Zemplen or similar conditions. The resultant nucleoside was converted to the nucleoside phosphoramidite using the monochloridite method.

The 2'-deoxynucleosides can be synthesized in a similar manner as described in Vaught et al., *J. Am. Chem. Soc*, 132(12):4141-4151 (2010) which are hereby incorporated by reference in their entireties.

Example 2

Preparation of 5'-O-DMTr-3'-O-Ac-5-(2-(N4-methylpiperazinylethyl) carbamoyl)-2'-O-methyluridine (2c)

In a 50 mL Boston Round Bottle was 5'-O-DMTr-3'-O-Ac-5-IodoUridine (1 g, 1.373 mmol) in THF (Volume: 10 ml) and DMA (Volume: 10 ml) to give a colorless solution. Tetrakis (triphenylphosphine)palladium(0) (0,159 g, 0.137 mmol) is weighed out and added to the bottle followed by addition of triethyiamine (0.694 g, 6.86 mmol) and 2-(4-methylpiperazin-1-yl)ethanamine (0.413 g, 2.88 mmol). The Bottle is placed into a 250 mL Parr Bomb, which is sealed and evacuated through the needle valve. The Bomb is then pressurized to 60 psi with Carbon Monoxide. The bomb is then evacuated under high vacuum and re-charged with Carbon Monoxide (60 psi). The bomb is resealed and placed in an oil bath heated to 70° C. For 17 h. The bomb is cooled to it and the pressure released slowly. The bottle is removed from the bomb and the solvent is removed in vacuo (Vaught et al., *J. Am. Chem. Soc.,* 132(12):4141-4151 (2010) which is hereby incorporated by reference in its entirety).

The dried product is re-dissolved in MeOH (10 mL) and 1 pellet of NaOH (~40 mg) is added along with a small stir bar. The bottle is fitted with a septum and the mixture is stirred at 50° C. overnight. TLC (3% TEA in Hexanes treated plate, 5% MeOH in DCM developing solvent, visualized via UV and Hannessians Stain w/charring) reveals a single trityl bearing product. The reaction mixture is concentrated to dryness and applied to a 80 g ISCO silica cartridge that is equilibrated with DCM and 1% TEA. The product is eluted from the column with a 0-10% MeOH in DCM (1% TEA) solvent gradient over 2 L @ 60 ml/min. The pure fractions are collected, combined and concentrated to dryness to give 5'-O-DMTr-3'-O-Ac-5-(2-(N4-methylpiperazinylethyl)carboxamidoUridine (0.93 g, 1.274 mmol, 93% yield) as a white foam. 1H NMR δ 2.33 (s, 3H), 2.50-2.65 (m, 10H); 3.44-3.52 (m, 4H); 3.54 (s, 3H); 3.79 (s, 6H); 3.87-3.92 (m, 1H); 4.00-4.08 (m, 1H); 4.10-4.17 (m, 1H); 5.90 (d, J=3.2 Hz, 1H); 6.85 (dd, J=9.0, 1.3 Hz, 4H); 7.27-7.49 (m, 9H); 8.52 (s, 1H); 8.77 (t, J=5.4 Hz, 1H). MS (ESI) M+1=730, calcd, 729.

Below are the experimental details for selected 5-carboxamido base modifications shown in FIG. 2. Each compound was synthesized in the same manner using the appropriate primary amine. All compounds gave yields between 60-95%.

Compound 2a, Propyl-Imidazole Derivative

Using 3 equivalents of 1-(3-aminopropyl)imidazole as the primary amine gave the desired product as an off white foam in 64% yield. $^1$H NMR (300 MHz) δ 2.00-2.10 (m, 2H); 3.21-3.37 (m, 2H), 3.46 (d, J=4.2 Hz, 2H), 3.57 (s, 3H), 3.78 (s, 6H), 3.92 (dd, J=5.6, 3.2 Hz, 1H), 3.95-4.10 (m, 4H), 4.15-4.22 (m, 1H), 5.92 (d, J=3.2 Hz, 1H), 6.08 (bs, 1H), 6.84 (dd, J=9.0, 1.4 Hz, 4H), 6.93-7.50 (m, 10H), 7.63 (s, 1H), 7.76 (s, 1H), 8.58 (s, 1H), 8.74 (t, J=6.0 Hz, 1H). MS (ESI+) calc'd 711.76. found 712.6.

Compound 2b, Propyl-Morpholine Derivative

Using 3 equivalents of 3-Morpholinopropylamine as the primary amine gave the desired product as a white foam in 64% yield. $^1$HNMR (300 MHz) δ 1.76 (quin, J=7.0 Hz, 2H), 2.41-2.50 (m, 4H), 3.40-3.47 (m, 4H), 3.53 (s, 3H), 3.70-3.75 (m, 8H), 3.79 (s, 6H), 3.89 (dd, J=5.7, 3.2 Hz, 1H), 3.98-4.15 (m, 2H), 5.90 (d, J=3.2 Hz, 1H), 6.84 (dd, J=9.0, 0.9 Hz, 4H), 7.15-7.48 (m, 9H), 8.48 (s, 1H), 8.75 (t, J=5.8 Hz, 1H). MS (ESI+) calc'd 730.8. found 731.5.

Compound 2e, Benzyl Derivative

Using 3 equivalents of benzylamine as the primary amine gave the desired product as a white foam in 87% yield. $^1$HNMR (300 MHz) δ 3.45-3.49 (m, 2H), 3.56 (s, 3H), 3.78 (s, 6H), 3.89 (dd, J=5.6, 3.1 Hz, 1H), 4.03-4.17 (m, 2H), 4.58 (dd, J=5.7, 4.6 Hz, 2H), 5.90 (d, J=3.1 Hz, 1H), 6.85 (dd, J=9.0, 1.3 Hz, 4H), 7.15-7.60 (m, 15H), 8.59 (s, 1H), 8.87 (t, J=5.9 Hz, 1H).

Compound 2h, 2-Ethyl-N,N-Dimethylamine Derivative

Using 3 equivalents of N,N-dimethylethylenediamine as the primary amine gave the desired product as a white foam in 91% yield. $^1$HNMR (300 MHz) δ 2.31 (s, 6H), 2.54 (t, J=6.5 Hz, 2H), 3.40-3.50 (m, 3H), 3.52 (s, 3H), 3.79 (s, 6H), 3.88 (dd, J=5.6, 3.1 Hz), 3.95-4.10 (m, 4H), 5.86 (d, J=3.1 Hz, 1H), 6.84 (dd, J=9.0, 1.4 Hz, 4H), 7.17-7.49 (m, 9H), 8.46 (s, 1H), 8.79 (t, J=5.6 Hz, 1H).

Example 3

Preparation of 5'-O-DMTr-5-((2-(N4-methylpiperazinylethyl)carbamoyl)-2'-O-methyluridine Amidite (3c)

In a 100 mL round-bottomed flask was DIEA (0.364 ml, 2.084 mmol) and 5-(3-(4-methylpiperazin-1-yl) propan-1-carboxamido)-5'-O-DMTr-3'-O-Ac-2'-O-Me-Uridine (1.55 g, 2.084 mmol) dissolved in DCM (Volume: 15 ml) to give a colorless solution. The flask was flushed with argon and set to stir. 3-((chloro(diisopropylamino)phosphine)oxy)propanenitrile (or "monochloridite") (0.451 g, 2.084 mmol) was added dropwise and the reaction mixture allowed to stir for 3 hours. TLC revealed that the reaction was complete. The reaction mixture was diluted with sat NaHCO$_3$ (100 mL) and the aqueous phase was extracted with DCM (3×50 mL). The organic phases were combined and dried with a brine wash (1×50 mL) and addition of Na$_2$SO$_4$. The organic phase was filtered and concentrated.

Purification was done via column chromatography on a 40 g silica cartridge pretreated with 3% TEA in Hexanes. Product was eluted with a 0-5% MeOH in DCM (over 1 L @ 40 mL/min). Pure fractions were combined and concentrated to give a white amorphous foam. The product was co-evaporated with DCM (3×30 mL) and dried under high vacuum overnight before use in automated oligonucleotide synthesis. 5'-O-DMTr-5-((2-(N4-methylpiperazinyiethyl) carbamoyl)-2'-O-methyluridine Amidite (1.47 g, 1.557 mmol, 74.7% yield). 1H NMR δ 1.15-1.25 (m, 12H): 2.31 (s, 3H); 2.36 (t, J=6.5 Hz, 2H); 2.41-2.69 (m, 12H); 3.34-3.72 (m, 9H); 3.76-4.06 (m, 8H); 4.18-4.36 (m, 1H); 5.90 (dd, J=5.4, 5.0 Hz, 1H); 6.80-6.92 (m, J=9.0, 4H); 7.15-7.51 (m, 9H); 8.51 (ds, 1H); 8.78-8.90 (m, 1H). MS (ESI) M+1=931, calcd, 930.

Experimental details for selected 5-carboxamido base modifications in FIG. 2. Each compound was synthesized in the same manner using 1.00 equivalents of 3-(((diisopropylamino)(methyl)phosphino)oxy)propanenitrile. All compounds gave yields between 75-95%.

Compound 3b, Phosphoramidite of Propyl-Morpholine Derivative

White foam obtained in 82% yield after column chromatography (DCM/MeOH/TEA), A 1:1 mixture (determined by $^1$H NMR) of diastereomers was measured by NMR. The protons that were resolved are described before the tabulated results and denoted by an asterisk. $^{31}$P NMR (121.5 MHz) δ 150.15*, 150.89*. In the proton spectra, the mixture gives rise to the following resolved diastereomeric peaks: A singlet at 3.45 ppm* and 3.47 ppm* corresponding to 3H of the 2'-O-methyl group; Two singlets at 3.80 ppm* and 3.81 ppm* correspond to 6H of the methoxy groups on the trityl; two doublets at 5.92 ppm* and 5.96 ppm* with coupling constants of 5.0 Hz and 5.4 Hz, respectively, and corresponding to 1H at the C1'-position; Two singlets at 8.49 ppm* and 8.56 ppm* corresponding to 1H at the C-6 position of the base. The balance of peaks are as follows: $^1$H-NMR (300 MHz) δ 1.04-1.22 (m, 12H), 1.69-1.82 (m, 2H), 2.41-2.49 (m, 6H), 2.58-2.67 (m, 2H), 3.33-3.44 (m, 4H), 3.51-3.65 (m, 3H), 3.70-3.76 (m, 4H), 3.83-3.95 (m, 1H), 3.95-4.07 (m, 1H), 4.17-4.36 (m, 2H), 6.82-6.89 (m, 4H), 7.15-7.51 (m, 9H), 8.63-8.76 (m, 1H). MS (ESI+) calc'd 931.0. found 931.8.

Compound 3a, Phosphoramidite of Propyl-Imidazole Derivative

White amorphous foam obtained in 80% yield after column chromatography (DCM/MeOH/TEA). A 55:45 mixture (determined by $^1$H NMR) of diastereomers was measured by NMR. The protons that were resolved are described before the tabulated results and denoted by an asterisk. $^{31}$P NMR (121.5 MHz) δ 150.26*, 150.81*. In the proton spectra, the mixture gives rise to the following resolved diastereomeric peaks: Two doublets of triplets with the major diastereomer at 2.63 ppm* (J=6.1, 1.3 Hz) and the minor signal at 2.37 (J=6.3, 1.4 Hz) corresponding to 2H; Two singlets, both at 3.49 ppm* correspond to 3H of the 2'-O-methyl groups; two doublets at 5.92 ppm*(minor, J=4.5 Hz) and 5.99 ppm* (major, J=5.2 Hz) corresponding to 1H at the C1'-position; Two singlets at 8.55 ppm* (major) and 8.63 ppm* (minor) corresponding to 1H at the C-6 position of the base. The balance of peaks are as follows: $^1$H-NMR (300 MHz) δ 1.04-1.22 (m, 12H), 1.97-2.10 (m, 2H), 2.80-2.94 (m, 1H), 3.23-3.47 (m, 4H), 3.52-3.74 (m, 3H), 3.75-3.95 (m, 7H), 3.96-4.13 (m, 3H), 4.22-

4.41 (m, 2H), 6.79-6.89 (m, 4H), 6.96 (s, 1H), 7.10 (s, 1H), 7.15-7.53 (m, 9H), 7.59 (s, 1H), 8.69-8.80 (m, 1H). MS (ESI+) calc'd 912.0. found 912.3.

Compound 3h, Phosphoramidite of 2-Ethyl-N,N-Dimethylamine Derivative

White amorphous foam, obtained in 87% yield after column chromatography (DCM/MeOH/TEA). A 55:45 mixture (determined by $^1$H NMR) of diastereomers was measured by NMR. The protons that were resolved are described before the tabulated results and denoted by an asterisk. $^{31}$P NMR (121.5 MHz) δ 150.12*, 150.71*. In the proton spectra, the mixture gives rise to the following resolved diastereomeric peaks: two doublets at 5.90 ppm* (minor, J=4.8 Hz) and 5.93 ppm* (major, J=5.2 Hz) corresponding to 1H at the C1'-position; Two singlets at 8.46 ppm* (major) and 8.53 ppm* (minor) corresponding to 1H at, the C-6 position of the base. The balance of peaks are as follows: $^1$H-NMR (300 MHz) δ 1.04-1.22 (m, 12H), 2.31 (s, 6H), 2.52-3.06 (m, 4H), 3.33-3.49 (m, 5H), 3.52-3.74 (m, 4H), 3.75-3.94 (m, 7H), 3.95-4.07 (m, 1H), 4.16-4.34 (m, 2H), 6.80-6.90 (m, 4H), 7.15-7.53 (m, 10H), 8.68-8.82 (m, 1H).

Compound 3e, Phosphoramidite of Benzyl Derivative

White amorphous foam obtained in 89% yield after column chromatography (EtOAc/Hex). A 55:45 mixture (determined by $^1$H NMR) of diastereomers was measured by NMR. The protons that were resolved are described before the tabulated results and denoted by an asterisk. $^{31}$P NMR (121.5 MHz) δ 150.26*, 150.81*. In the proton spectra, the mixture gives rise to the following resolved diastereomeric peaks: Two doublets of triplets with the major diastereomer at 2.64 ppm* (J=6.5, 2.1 Hz) and the minor signal at 2.38 (J=6.5, 1.5 Hz) corresponding to 2H; Two doublets at 5.93 ppm*(minor, J=4.7 Hz) and 5.98 ppm* (major, J=5.3 Hz) corresponding to 1H at the C1'-position; Two singlets at 8.57 ppm* (major) and 8.64 ppm* (minor) corresponding to 1H at the C-6 position of the base. The balance of peaks are as follows: $^1$H-NMR (300 MHz) δ 1.04-1.22 (m, 12H), 3.36-3.46 (m, 2H), 3.50-3.76 (m, 4H), 3.77-3.93 (m, 7H), 3.95-4.10 (m, 1H), 4.17-4.36 (m, 2H), 4.45-4.67 (m, 2H), 6.82-6.90 (m, 4H), 7.15-7.54 (m, 14H), 8.83-8.95 (m, 1H). MS (ESI+) calc'd 912.0. found 912.3.

Example 4

General Synthetic Methodology of Truncated Nucleotides

Carboxamido-substituents for modifications were chosen from both hydrophilic and hydrophobic groups. Hydrophilic groups were preferentially chosen for the following reasons: Their ability to create new hydrogen bonding interactions with other nucleobases; the lack of exchangeable protons or sensitive functional groups that would require extra protecting groups under standard oligonucleotide synthesis; the cationic nature of these groups at physiological pH. Hydrophobic groups were chosen to attempt to exploit pi-stacking interactions between nucleobases and to create new hydrophobic regions in the nucleotide. Creating new hydrophobic and cationic/hydrophilic regions on a nucleotide may also create enhanced binding to serum proteins that enhance cell permeability. Pendant hydrophobic groups (such as sterols and straight chain lipids) as well as nucleotides with 2'-hydrophobic modifications (such as alkyl, aryl and 2'-4'-linkers) can enhance cellular uptake by increasing interaction with serum lipoprotein particles. Likewise, counteracting the very anionic nucleotide backbone with highly charged cationic species also enhances cellular uptake.

Short strands of oligonucleotides bearing sugar and base modifications can be prepared once the modified nucleoside is synthesized and the free 5' and 3'-hydroxyl groups are masked with appropriate reactive groups to become a nucleotide monomer. The current state of the art in oligonucleotide synthesis is automated solid phase synthesis using phosphoramidite chemistry, which, in particular, is based on the developments of McBride et al., *Tetrahedron Letters* 24:245-248 (1983) and Sinha et al., *Tetrahedron Letters* 24:5843-5846 (1983). Phosphoramidite chemistry, together with related methods such as hydrogen phosphonate chemistry, has been extensively reviewed with respect to their uses in oligonucleotide chemistry by Beaucage et al., *Tetrahedron* 48:2223-2311 (1992). During solid phase oligonucleotide synthesis, a series of nucleotide monomers are sequentially attached, via their phosphoramidite derivatives, in a predetermined order to either, depending on the direction of chain extension, the 5'-functional group or the 3'-functional group of the growing oligonucleotide strand.

The oligonucleotide strand is anchored to an insoluble moiety such as controlled pore glass or polystyrene resin beads. The method of attachment of each monomer is generally comprised of the following steps 1-5. Step 1 involves the protection of the reactive functionality. The common reactive functionality is the 5'-hydroxyl group of the terminal nucleoside. This functionality is usually protected with a 4,4'-dimethoxytrityl (DMT) moiety that can be removed via acid treatment. One of the attractive features of the DMT moiety is that it forms a bright orange DMT cation during acid deprotection. This cation serves effectively as reporter group that can be easily monitored at a wavelength between 480 and 500 nm for the purpose of judging the completeness the previous coupling step. Most commercially available automated synthesizers have the capability to monitor the released DMT cation. This data gives the operator an instant indication of whether or not the synthesis failed at any given step. Step 2 involves the coupling by addition of a phosphoramidite derivative and an activator. The phosphoramidite derivative is usually a nucleoside phosphoramidite, however, it may also be a phosphoramidite derivatized with a different organic moiety. Step 3 involves the capping of unreacted terminal functional groups. This step introduces an inert protective group that prevents further coupling to failure sequences. Step 4 involves oxidation of the newly formed phosphorous nucleotide backbone linkage from the trivalent phosphite to the stable pentavalent state. This oxidation step can be performed with either an oxygen-based oxidant that results in a phosphate nucleotide or a sulfurizing oxidant that results in a phosphorothioate nucleotide. Step 5 involves a repetition of the process the after a washing step.

Truncated, 16 nucleotide sequence complementary to a nucleotide sequence of human miR-208a was synthesized in 1 µmol scale on an ABI Expedite 8909 Automated Nucleic Acid Synthesis System. The synthesizer was operated using standard detritylation and capping solutions, known to those skilled in the art, single couplings of 420 seconds for each base and oxidation with 0.2M PADS oxidation solution after each coupling cycle. The unmodified anti-208a RNA sequence incorporates nine uridine residues which were fully replaced with nine modified nucleobases. The balance of the nucleotides were comprised of 2'-O-methyl-nucleotides. One exception was the incorporation of oleylcarboxamido derivative, where there is a single incorporation on base position 15 of 16 where the nucleoside amidite was incorporated via a double coupling of 420 seconds each.

Example 5

Preparation of Oligonucleotide miRNA Inhibitors

Preparation of compound 10941 (mCs;ppTs;ppTs;ppTs;ppTs;ppTs;mGs;mCs;ppTs;mCs;mGs;ppTs;mCs;ppTs;ppTs;mA). Phosphoramidite Reagent (3c) in the Synthesis of the Base Modified Oligonucleotide was used. The oligodeoxynucleotide was synthesized using an ABI Expedite (Model 8909) DNA/RNA synthesizer. The synthesis was performed according to the manufacturer's recommendations in DMT-ON mode employing commercial synthesis reagents, exchanging 0.2M PADS in 1:1 Pyridine/ACN for the oxidizing solution. The phosphoramidite reagent was added as a 0.1 M solution in acetonitrile during the appropriate coupling cycle. The cleavage of the oligonucleotide from the support was accomplished either by the method of described in U.S. Pat. No. 5,750,672 (which is hereby incorporated by reference in its entirety) or via heating of the CPG bound oligonucleotide with a solution of 40% aqueous methyl amine at 55° C. for 30 minutes. The resultant aqueous solution of oligonucleotide was further purified by loading the crude DMT-ON oligonucleotide solution on a Waters Sep-Pak® Vac C18 cartridge and eluting using a standard DMT-ON oligonucleotide desalting procedure known to those knowledgeable in the art. The characterization of product was performed by MALDI-TOF mass spectrometry utilizing 3-hydroxypicolinic acid as matrix and standard methods known to those knowledgeable in the art: calcd 6922.4. found 6920.7.

Compound M-10708 (FIG. 5) was synthesized with amidite 3e in the uridine position in exactly the manner described above. The characterization of product was performed by ESI mass spectrometry on a Waters SQD mass detector in 200 mM HFIP/8.15 mM TEA buffer gradient with MeOH: calcd 6597.6. found 6599.1.

Compound M-10713 (FIG. 5) was synthesized with amidite 3f in the uridine position in exactly the manner described above. The characterization of product was performed by ESI mass spectrometry on a Waters SQD mass detector in 200 mM HFIP/8.15 mM TEA buffer gradient with MeOH: calcd 6543.9. found 6543.9.

Compound M-10711 (FIG. 5) was synthesized with amidite 3a in the uridine position in exactly the manner described above. The characterization of product was performed by ESI mass spectrometry (negative mode) on a Waters SQD mass detector in 200 mM HFIP/8.15 mM TEA buffer gradient with MeOH: calcd 6759.8. found 6759.6.

Compound M-10712 (FIG. 5) was synthesized with amidite 3d in the uridine position in exactly the manner described above. The characterization of product was performed by ESI mass spectrometry (negative mode) on a Waters SQD mass detector in 200 mM HFIP/8.15 mM TEA buffer gradient with MeOH: calcd 6759.8. found 6760.6.

Compound M-10768 (FIG. 5) was synthesized with 2'-O-methyluridine in its amidite position and amidite 3d in the auxiliary amidite position in exactly the manner described above. The characterization of product was performed by ESI mass spectrometry (negative mode) on a Waters SQD mass detector in 200 mM HFIP/8.15 mM TEA buffer gradient with MeOH: calcd 6003.9. found 6005.2.

Compound M-10772 (FIG. 5) was synthesized with amidite 3i in the uridine position in exactly the manner described above. The characterization of product was performed by ESI mass spectrometry (negative mode) on a Waters SQD mass detector in 200 mM HFIP/8.15 mM TEA buffer gradient with MeOH: calcd 6552.8. found 6553.4.

Compound M-10774 (FIG. 5) was synthesized with 2'-O-methyluridine in its amidite position and amidite 3i in the auxiliary amidite position in exactly the manner described above. The characterization of product was performed by ESI mass spectrometry (negative mode) on a Waters SQL) mass detector in 200 mM HFIP/8.15 mM TEA buffer gradient with MeOH: calcd 5912.0. found 5912.8.

Compound M-10876 (FIG. 5) was synthesized with amidite 3b in the uridine position in exactly the manner described above. The characterization of product was performed by ESI mass spectrometry (negative mode) on a Waters SQD mass detector in 200 mM HFIP/8.15 mM TEA buffer gradient with MeOH: calcd 6931.2. found 6931.9.

Compound M-10877 (FIG. 5) was synthesized with amidite 3b in the uridine position and amidite 3g in an auxiliary amidite position on the ABI Expedite (Model 8909) DNA/RNA synthesizer. The oligonucleotide was handled in exactly the manner described above, except amidite 3g was the first coupling to 2'-O-Me-adenosine functionalized CPG. Incorporation of 3g is denoted by the precursor "y" in FIG. 5. The characterization of product was performed by ESI mass spectrometry (negative mode) on a Waters SQD mass detector in 200 mM HFIP/8.15 mM TEA buffer gradient with MeOH: calcd 7056.0. found 7056.5.

Compound M-10878 (FIG. 5) was synthesized with 2'-O-methyluridine in its amidite position and amidite 3b in the auxiliary amidite position in exactly the manner described above. The characterization of product was performed by ESI mass spectrometry (negative mode) on a Waters SQD mass detector in 200 mM HFIP/8.15 mM TEA buffer gradient with MeOH: calcd 6080.1. found 6081.

Compound M-10881 (FIG. 5) was synthesized with 2'-O-methyluridine in its amidite position and amidite 3b in the auxiliary amidite position in exactly the manner described above. The characterization of product was performed by ESI mass spectrometry (negative mode) on a Waters SQD mass detector in 200 mM HFIP/8.15 mM TEA buffer gradient with MeOH: calcd 6250.3. found 6251.5.

Example 6

Determination of Melting Temperature

Melting temperature ($T_m$) enhancement was determined on a per incorporation basis by determining the difference between the melting temperature of the modified strand and that of the identical sequence utilizing either a phosphorothioate DNA nucleotide or a phosphorothioate 2'-O-methyl RNA nucleotide.

For example, the modified anti-208a oligonucleotides were annealed to the complementary sequence, twenty-two nucleotides in length, comprised of RNA nucleosides and a phosphate backbone. The complementary sequence was identical to the endogenous miRNA. Thermal denaturation temperatures ($T_m$) were measured as a maximum of the first derivative plot of melting curvex (A260 vs. Temp). The duplexes were constituted at 1 µM in a 0.9% NaCl buffer. Temperature was ramped from 25° C. to 95° C. at 4° C./min and OD's at 260 nm were read once per minute, $T_m$ values are averages of at least two measurements.

Duplex Melting Temperatures for Various Modifications of a 16 Nucleotide Sequence Complementary to a Nucleotide Sequence of Human miR-208a.

Modifications included a mixed 9 LNA/7 DNA phosphorothioate, fully substituted 2'-O-methyl-nucleotide phosphorothioate, fully 2'-deoxynucleotide phosphorothioate and various substitution patterns of fully 2'-O-methyl-nucleotides with 5-carboxamide substituents. While hydrophobic substitutions did not provide substantial gains in affinity enhancement versus the unmodified 2'-O-methyl parent compound, all of the cationic species provided significant duplex stabilization on the order of 2-3° C./Modification over the unmodified 2'-OMe nucleotide. Duplexes were constituted at 1 µM in 0.9% NaCl. Temperature was ramped from 25° C. to 95° C. at 4° C./min and OD's at 260 nm were read once per minute on a Cary 100 Bio UV-Visible Spectrophotometer. See FIG. 4 and FIG. 5.

Example 7

Cardiomyocytes Data

Cell culture experiments conducted with primary neonatal rat cardiomyocytes demonstrate that many of the 5-carboxamido-base modified oligonucleotides not only bind to miR-208a, but also effect the downstream regulation of bMHC in a manner expected for effective, intracellular miR-208a inhibitors. As shown in FIGS. 6 and 7, two known positive controls that contain LNA/DNA or LNA/2'-O-Me mixtures of nucleotides show both miR-208a inhibition and a dose dependent regulation of bMHC. All oligonucleotides were passively (no transfection reagent) put onto the cells in 2% serum containing media. The cells were lysed using Cells to Ct (Ambion) buffer after 72 hour incubation at 37° C. MiR-208a and the mRNA bMHC were analyzed by Taqman based RT-PCR (Applied Biosystems). All experiments were performed in triplicate and shown as average +/−standard deviation. Base modifications that feature pendant cationic species with pKa values in the 7-8 range, those most likely to be mostly protonated at physiological pH, were more likely to show a positive correlation between miR-208a inhibition and bMHC. This correlation suggests that the miR-208a inhibition occurs pre-lysis of the primary cardiomyocytes. It should also be noted that nucleotide substitution patterns can affect the potency of inhibitors having the same sequence. The 5-(2-(2-methyl-1H-imidazol-1-yl)-ethylcarboxamido)-2'-O-methyluridine nucleotide variant shows inhibition of miR-208a when incorporated in a 16-nucleotide 2'-O-methyl phosphorothioate anti-208a nucleotide sequence where either 4 or 9 of the total 9 natural uridine nucleotide positions are substituted. It is only the oligonucleotide that has 4 substitutions that shows effective bMHC mRNA regulation.

Example 8

In Vivo Testing

Three base modified oligonucleotides were studied in vivo in C57BL/6 mice (10941, 10876, 10711). A scrambled control containing the comparable bases of each oligo were also injected (11091, 11087, 11086). The oligonucleotides were dosed with a 25 mg/kg delivered via subcutaneous injection on Day 1. Cardiac tissue was harvested 4 days after dosing and miR-208a levels were determined via real time PCR. There was neither injection site reaction nor any visible organ damage following take down of the mice. As seen in FIG. 8, all targeting oligos showed some inhibition of miR-208a, and the 10711 oligonucleotide was able to inhibit miR 208a, in cardiac tissue in a statistically significant, manner compared to saline. None of the controls were statistically different than saline. This demonstrated the ability of systemically administered base modified oligonucleotides to act as potent inhibitors of cardiac specific miRNA's without the use of conjugates or drug delivery systems.

Example 9

$T_m$ Differences Between 2'-deoxy and 2'-O-Me Base Modifications $T_m$ Effects of Both Base and Sugar Modifications when Visualized on a Scale from Least Modified to Most Modified Base modifications alone are expected to have only a modest effect on 2'-deoxyribonucleosides with phosphate backbones (see examples of Ahmadian et al., *Nucleic Acids Res.*, 1998, 26(13):3127-3135 (1998); Znosko et al., *J. Am. Chem. Soc.*, 125(20):6090-6097 (2003) which are hereby incorporated by reference in their entireties), and even then, substituents larger than C3-alkynes tend to destabilize DNA:DNA duplex stabilities. Even multiple incorporations of uridine based nucleosides with non-caxboxamido-linked hexylamines, protonated under physiological pH, showed no net DNA:DNA duplex stabilization (see Hashimoto et al., *J. Am. Chem. Soc.*, 115(16):7128-7134 (1993) which is hereby incorporated by reference in its entirety). Sugar modifications, in this case, 2'-O-methylated ribonucleosides, have been shown in our hands to stabilize this particular duplex with miR-208a RNA at about 1° C./modification. The 2'-deoxynucleosides with base modifications taught in this invention, when fully incorporated (9-substitutions for uridine) in a 16-mer, anti-208a oligonucleotide with a phosphorothioate backbone, give little increased duplex stabilization against miR-208a RNA. See FIG. 9. However, when the base modified 2'-deoxynucleosides were incorporated into a nucleotide that also contained 2'-O-methylated nucleosides for all bases excluding uridine, the stabilization of the base modification became apparent. Even though there were nine fewer sugar modifications, the duplex had the same $T_m$ as the oligonucleotide with sixteen 2'-O-methyl sugar modifications. 2'-O-Methylated anti-208a substituting each uridine with a uridine-based nucleoside that have both a 5-carboxamido-base modification and a 2'-O-methyl sugar modification show an unexpected increase in $T_m$ of more than 2° C./modification over the oligonucleotide with just sugar modifications.

These enhanced affinities likely are greatest when coupled with A-form nucleosides that have a 3'-endo sugar pucker. This effect may be more pronounced when the 5-carboxamido modified base is combined with 2'-4'-bridged bicyclic nucleoside sugar that locks the ribose in the A-form with a pronounced 3'-endo sugar pucker.

Example 10

Figure 9:
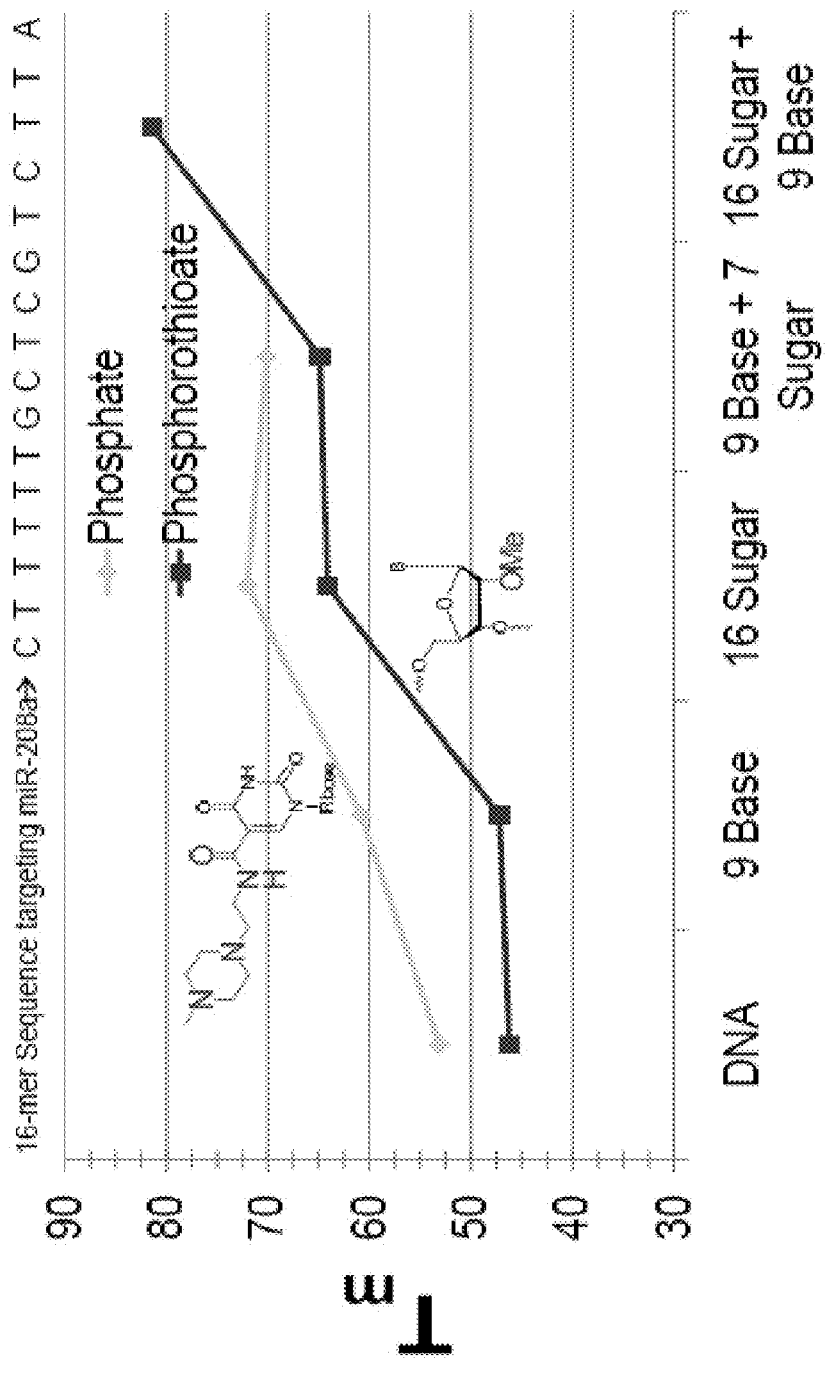
FIG. 9 shows the cumulative effect of base and sugar modifications, with both phosphate and phosphorothioate backbones.
Figure 10:
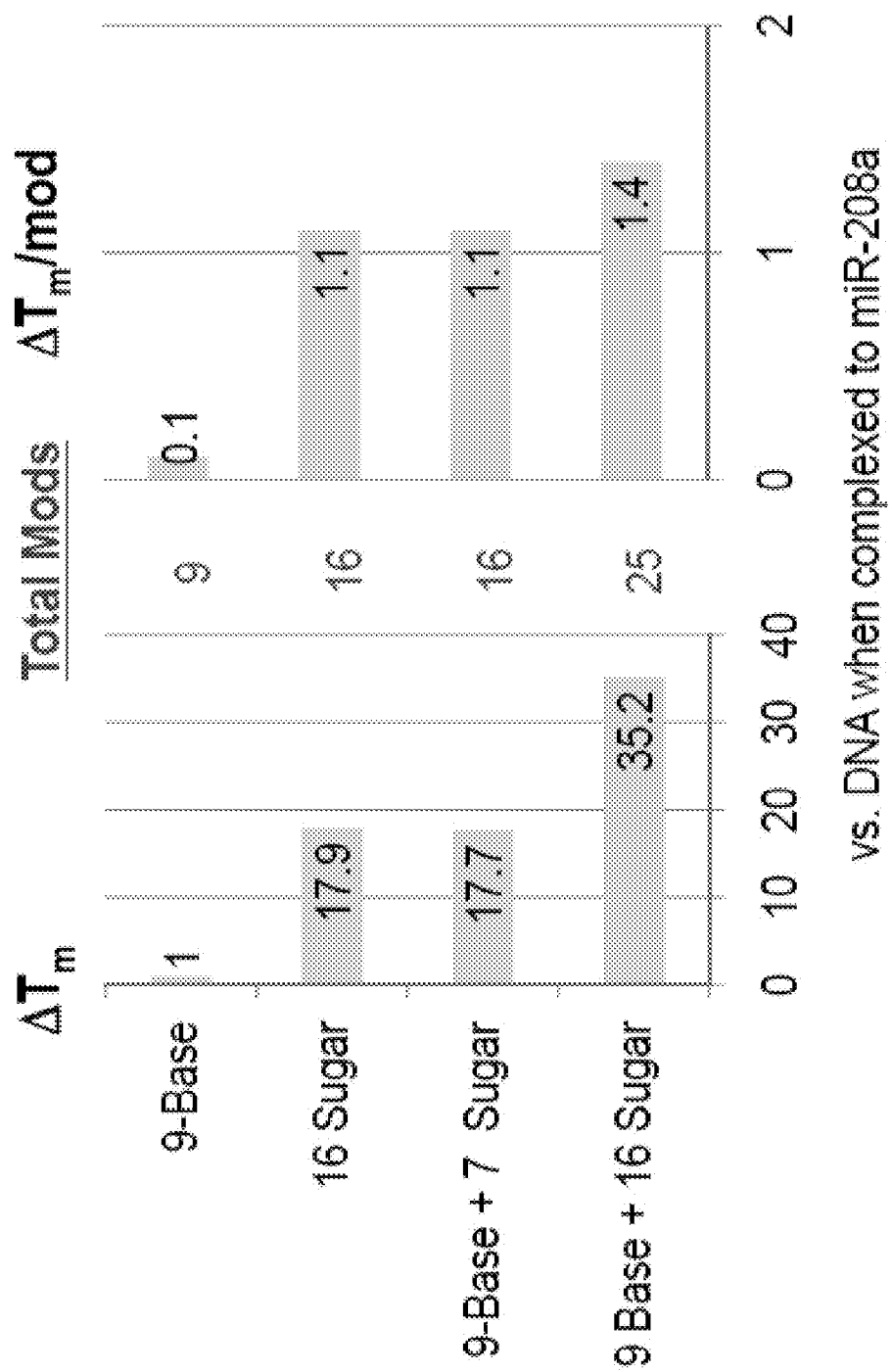
FIG. 10 is a graph of $\Delta T_m$ against number of base modifications and 2' modifications, and shows the synergistic effect.

Synergistic Effect of 5-Carboxamido- and 2'-O-Methyl Modifications is the Nucleotide FIG. 10 presents data from FIG. 9 as $\Delta T_m$/per modification, counting both sugar and base modifications. Multiple incorporations of 5-carboxyamido-2'-O-methyluridine nucleosides unexpectedly give a greater stabilization per sugar and base modification than either the base or sugar do alone. This evidence indicates that 5-carboxamido in conjunction with modifications that favor a 3'-endo sugar pucker of nucleosides are more than additive. They work synergistically to give greater duplex stability than either modification alone. Increased duplex stability, subject to limits, is likely desirable for certain oligonucleotide based therapeutics, such as microRNA inhibitors. Furthermore, these types of modifications may also protect from enzymatic degradation, cellular delivery due to decreased electrostatic charge and enhanced pharmacokinetic and/or pharmacodynamic properties.

Example 11

Figure 11:
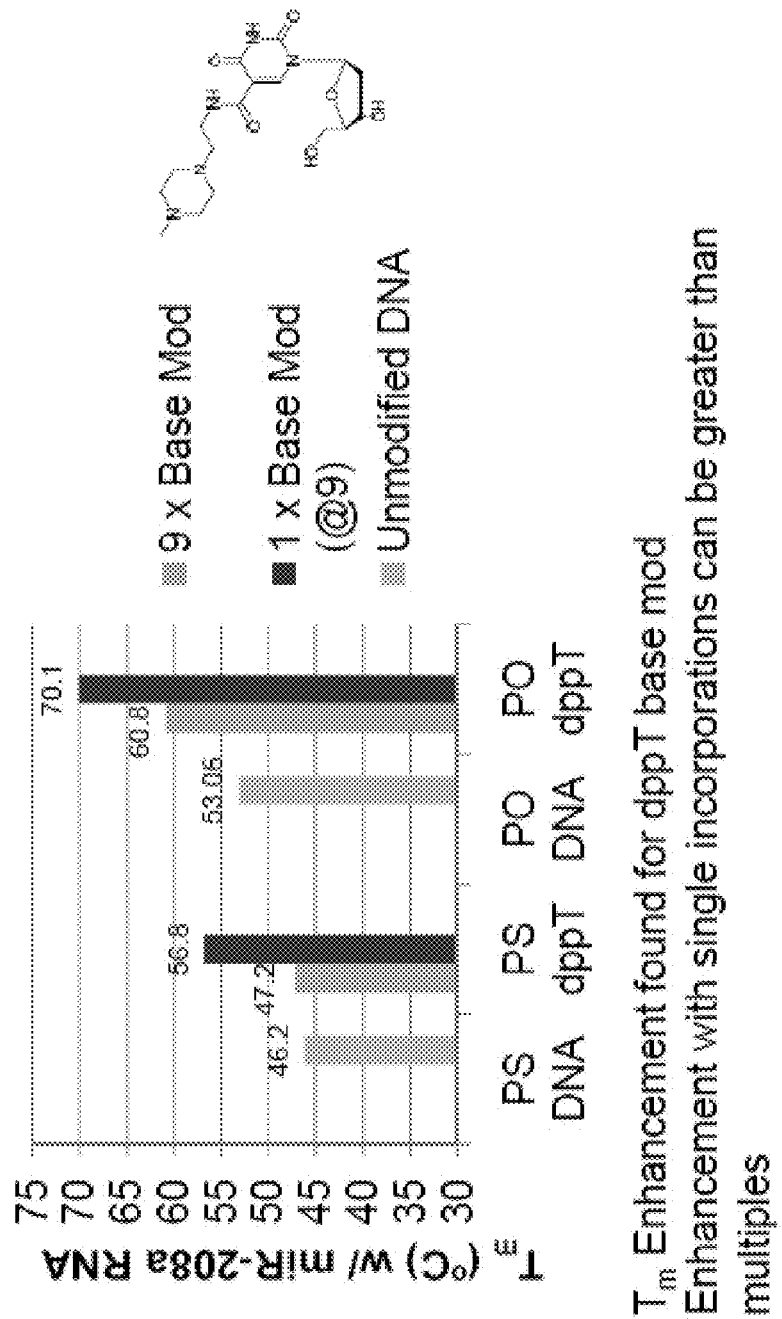
FIG. 11 is a graph of $T_m$ effect of a select base modification with respect to number of modifications and backbone chemistry.

Effect of Multiple Incorporations of Base Modified Nucleotides in the Oligonucleotide Multiple incorporations (i.e. 9 bases out of 16 total) of a cationic 5-carboxamido-modified deoxyuridine seems to give minimal boosts to duplex stability for both phosphorothioate and phosphate backbone 16-mer oligonucleotides. See FIG. 11. This may be due to perturbations in hydrating the bases or steric bulk of the substituents. It is surprising to note, though, that a single incorporation can increase the duplex stability of a 16-mer anti-208a deoxyoligonucleotide with either phosphorothioate or phosphate backbones with its target, miR-208a RNA, by more than 10° C. and 17° C., respectively. The modifications disclosed in this invention can be used alone, as single or multiple incorporations, or in conjunction with other sugar modifications, as single or multiple incorporations, to obtain a therapeutic oligonucleotide with desirable duplexing properties, duplex-protein binding properties, or along with desirable pharmacokinetic and/or pharmacodynamic properties.

Although preferred embodiments have been depicted and described in detail herein, it will be apparent to those skilled in the relevant art that various modifications, additions, substitutions, and the like can be made without departing from the spirit of the invention and these are therefore considered within the scope of the present invention as defined in the claims which follow.

The invention claimed is:

1. A base modified antisense oligonucleotide, comprising: at least one nucleotide having both:
   a) a 2' modification; and
   b) an amino carbonyl base modification at the C-5 position of a pyrimidine base,
   wherein the oligonucleotide is from about 5 to about 25 nucleotides in length and contains one or more phosphorothioate linkages; and
   wherein the 2' modification is 2'-OMe and the amino carbonyl modified pyrimidine base has the following structure:

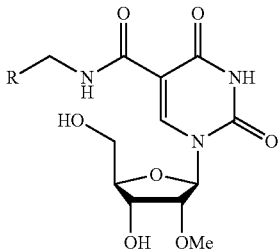

wherein R is at least one member selected from the group consisting of:

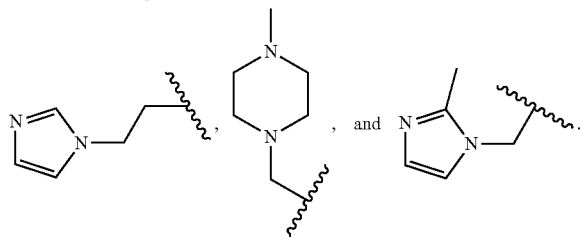

2. The base modified antisense oligonucleotide of claim 1, wherein the oligonucleotide hybridizes to a human microRNA with high affinity.

3. The base modified antisense oligonucleotide of claim 1, wherein the oligonucleotide is from about 10 to about 18 nucleotides in length.

4. The base modified antisense oligonucleotide of claim 1, comprising: 2 or more nucleotides having both the 2' modification and the amino carbonyl modified base.

5. The base modified antisense oligonucleotide of claim 1, having from 2 to about 10 nucleotides having both the 2' modification and the amino carbonyl modified base.

6. The base modified antisense oligonucleotide of claim 1, wherein the oligonucleotide has one or more 2' deoxy nucleotides.

7. The base modified antisense oligonucleotide of claim 1, having a 5' and/or 3' cap structure.

8. The base modified antisense oligonucleotide of claim 1, wherein the oligonucleotide sequence is substantially complementary to the full length sequence of miR-208a, miR-208b, miR-15b, or miR-21.

9. The base modified antisense oligonucleotide of claim 1, wherein the oligonucleotide sequence is substantially complementary to the full length sequence of a human miRNA listed in Table 1.

10. A pharmaceutical composition, comprising:
   a) an effective amount of the base modified antisense oligonucleotide of claim 1, or a pharmaceutically acceptable salt thereof; and
   b) a pharmaceutically acceptable carrier or diluent.

11. The base modified antisense oligonucleotide of claim 1, wherein the oligonucleotide is fully phosphorothioate-linked.

12. The base modified antisense oligonucleotide of claim 1, wherein the amino carbonyl base modification is an amino carbonyl modified uracil or thymine base at the C-5 position.

13. The base modified antisense oligonucleotide of claim 1, wherein the amino carbonyl base modification is an amino carbonyl modified uracil at the C-5 position.

14. The base modified antisense oligonucleotide of claim 1, wherein R is

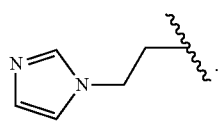

15. The base modified antisense oligonucleotide of claim 1, wherein R is

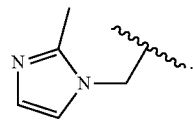

16. The base modified antisense oligonucleotide of claim 1, wherein R is

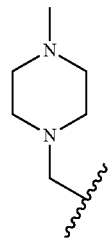

* * * * *

```
                         SEQUENCE LISTING

<160> NUMBER OF SEQ ID NOS: 81

<210> SEQ ID NO 1
<211> LENGTH: 22
<212> TYPE: RNA
<213> ORGANISM: Homo sapiens

<400> SEQUENCE: 1
uggaauguaa agaaguaugu au                                                  22

<210> SEQ ID NO 2
<211> LENGTH: 22
<212> TYPE: RNA
<213> ORGANISM: Homo sapiens

<400> SEQUENCE: 2
aacccguaga uccgaacuug ug                                                  22

<210> SEQ ID NO 3
<211> LENGTH: 23
<212> TYPE: RNA
<213> ORGANISM: Homo sapiens

<400> SEQUENCE: 3
uacccuguag aaccgaauuu gug                                                 23

<210> SEQ ID NO 4
<211> LENGTH: 22
<212> TYPE: RNA
<213> ORGANISM: Homo sapiens

<400> SEQUENCE: 4
ucccugagac ccuaacuugu ga                                                  22

<210> SEQ ID NO 5
<211> LENGTH: 21
<212> TYPE: RNA
<213> ORGANISM: Homo sapiens

<400> SEQUENCE: 5
ucacagugaa ccggucucuu u                                                   21

<210> SEQ ID NO 6
<211> LENGTH: 22
<212> TYPE: RNA
<213> ORGANISM: Homo sapiens
```

-continued

```
<400> SEQUENCE: 6
uuuggucccc uucaaccagc ug                                            22

<210> SEQ ID NO 7
<211> LENGTH: 22
<212> TYPE: RNA
<213> ORGANISM: Homo sapiens

<400> SEQUENCE: 7
uuuggucccc uucaaccagc ua                                            22

<210> SEQ ID NO 8
<211> LENGTH: 22
<212> TYPE: RNA
<213> ORGANISM: Homo sapiens

<400> SEQUENCE: 8
ucuacagugc acgugucucc ag                                            22

<210> SEQ ID NO 9
<211> LENGTH: 21
<212> TYPE: RNA
<213> ORGANISM: Homo sapiens

<400> SEQUENCE: 9
ugagaugaag cacuguagcu c                                             21

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                           23

<210> SEQ ID NO 11
<211> LENGTH: 22
<212> TYPE: RNA
<213> ORGANISM: Homo sapiens

<400> SEQUENCE: 11
ucucccaacc cuuguaccag ug                                            22

<210> SEQ ID NO 12
<211> LENGTH: 22
<212> TYPE: RNA
<213> ORGANISM: Homo sapiens

<400> SEQUENCE: 12
uagcagcaca uaaugguuug ug                                            22

<210> SEQ ID NO 13
<211> LENGTH: 22
<212> TYPE: RNA
<213> ORGANISM: Homo sapiens

<400> SEQUENCE: 13
uagcagcaca ucaugguuua ca                                            22

<210> SEQ ID NO 14
<211> LENGTH: 22
<212> TYPE: RNA
<213> ORGANISM: Homo sapiens
```

```
<400> SEQUENCE: 14
uagcagcacg uaaauauugg cg                                        22

<210> SEQ ID NO 15
<211> LENGTH: 23
<212> TYPE: RNA
<213> ORGANISM: Homo sapiens

<400> SEQUENCE: 15
aacauucauu gcugucggug ggu                                       23

<210> SEQ ID NO 16
<211> LENGTH: 21
<212> TYPE: RNA
<213> ORGANISM: Homo sapiens

<400> SEQUENCE: 16
uagcagcaca gaaauauugg c                                         21

<210> SEQ ID NO 17
<211> LENGTH: 22
<212> TYPE: RNA
<213> ORGANISM: Homo sapiens

<400> SEQUENCE: 17
uucaccaccu ucuccaccca gc                                        22

<210> SEQ ID NO 18
<211> LENGTH: 23
<212> TYPE: RNA
<213> ORGANISM: Homo sapiens

<400> SEQUENCE: 18
cccaguguuc agacuaccug uuc                                       23

<210> SEQ ID NO 19
<211> LENGTH: 23
<212> TYPE: RNA
<213> ORGANISM: Homo sapiens

<400> SEQUENCE: 19
cccaguguuu agacuaucug uuc                                       23

<210> SEQ ID NO 20
<211> LENGTH: 22
<212> TYPE: RNA
<213> ORGANISM: Homo sapiens

<400> SEQUENCE: 20
acaguagucu gcacauuggu ua                                        22

<210> SEQ ID NO 21
<211> LENGTH: 22
<212> TYPE: RNA
<213> ORGANISM: Homo sapiens

<400> SEQUENCE: 21
uggaauguaa ggaagugugu gg                                        22

<210> SEQ ID NO 22
<211> LENGTH: 22
<212> TYPE: RNA
<213> ORGANISM: Homo sapiens
```

```
<400> SEQUENCE: 22
auaagacgag caaaaagcuu gu                                              22

<210> SEQ ID NO 23
<211> LENGTH: 22
<212> TYPE: RNA
<213> ORGANISM: Homo sapiens

<400> SEQUENCE: 23
auaagacgaa caaaagguuu gu                                              22

<210> SEQ ID NO 24
<211> LENGTH: 23
<212> TYPE: RNA
<213> ORGANISM: Homo sapiens

<400> SEQUENCE: 24
uaaagugcuu auagugcagg uag                                             23

<210> SEQ ID NO 25
<211> LENGTH: 22
<212> TYPE: RNA
<213> ORGANISM: Homo sapiens

<400> SEQUENCE: 25
uagcuuauca gacugauguu ga                                              22

<210> SEQ ID NO 26
<211> LENGTH: 22
<212> TYPE: RNA
<213> ORGANISM: Homo sapiens

<400> SEQUENCE: 26
acagcaggca cagacaggca gu                                              22

<210> SEQ ID NO 27
<211> LENGTH: 22
<212> TYPE: RNA
<213> ORGANISM: Homo sapiens

<400> SEQUENCE: 27
aagcugccag uugaagaacu gu                                              22

<210> SEQ ID NO 28
<211> LENGTH: 23
<212> TYPE: RNA
<213> ORGANISM: Homo sapiens

<400> SEQUENCE: 28
agcuacauug ucugcugggu uuc                                             23

<210> SEQ ID NO 29
<211> LENGTH: 21
<212> TYPE: RNA
<213> ORGANISM: Homo sapiens

<400> SEQUENCE: 29
agcuacaucu ggcuacuggg u                                               21

<210> SEQ ID NO 30
<211> LENGTH: 21
<212> TYPE: RNA
<213> ORGANISM: Homo sapiens
```

```
<400> SEQUENCE: 30
caagucacua gugguuccgu u                                              21

<210> SEQ ID NO 31
<211> LENGTH: 21
<212> TYPE: RNA
<213> ORGANISM: Homo sapiens

<400> SEQUENCE: 31
aucacauugc cagggauuuc c                                              21

<210> SEQ ID NO 32
<211> LENGTH: 22
<212> TYPE: RNA
<213> ORGANISM: Homo sapiens

<400> SEQUENCE: 32
uucaaguaau ccaggauagg cu                                             22

<210> SEQ ID NO 33
<211> LENGTH: 21
<212> TYPE: RNA
<213> ORGANISM: Homo sapiens

<400> SEQUENCE: 33
uucaaguaau ucaggauagg u                                              21

<210> SEQ ID NO 34
<211> LENGTH: 22
<212> TYPE: RNA
<213> ORGANISM: Homo sapiens

<400> SEQUENCE: 34
aaggagcuca cagucuauug ag                                             22

<210> SEQ ID NO 35
<211> LENGTH: 22
<212> TYPE: RNA
<213> ORGANISM: Homo sapiens

<400> SEQUENCE: 35
uagcaccauc ugaaaucggu ua                                             22

<210> SEQ ID NO 36
<211> LENGTH: 23
<212> TYPE: RNA
<213> ORGANISM: Homo sapiens

<400> SEQUENCE: 36
uagcaccauu ugaaaucagu guu                                            23

<210> SEQ ID NO 37
<211> LENGTH: 22
<212> TYPE: RNA
<213> ORGANISM: Homo sapiens

<400> SEQUENCE: 37
uagcaccauu ugaaaucggu ua                                             22

<210> SEQ ID NO 38
<211> LENGTH: 22
<212> TYPE: RNA
<213> ORGANISM: Homo sapiens
```

<400> SEQUENCE: 38
uguaaacauc cucgacugga ag                                              22

<210> SEQ ID NO 39
<211> LENGTH: 22
<212> TYPE: RNA
<213> ORGANISM: Homo sapiens

<400> SEQUENCE: 39
uguaaacauc cuacacucag cu                                              22

<210> SEQ ID NO 40
<211> LENGTH: 23
<212> TYPE: RNA
<213> ORGANISM: Homo sapiens

<400> SEQUENCE: 40
uguaaacauc cuacacucuc agc                                             23

<210> SEQ ID NO 41
<211> LENGTH: 22
<212> TYPE: RNA
<213> ORGANISM: Homo sapiens

<400> SEQUENCE: 41
uguaaacauc cccgacugga ag                                              22

<210> SEQ ID NO 42
<211> LENGTH: 22
<212> TYPE: RNA
<213> ORGANISM: Homo sapiens

<400> SEQUENCE: 42
uguaaacauc cuugacugga ag                                              22

<210> SEQ ID NO 43
<211> LENGTH: 23
<212> TYPE: RNA
<213> ORGANISM: Homo sapiens

<400> SEQUENCE: 43
ucucacacag aaaucgcacc cgu                                             23

<210> SEQ ID NO 44
<211> LENGTH: 22
<212> TYPE: RNA
<213> ORGANISM: Homo sapiens

<400> SEQUENCE: 44
gaaguuguuc gugguggauu cg                                              22

<210> SEQ ID NO 45
<211> LENGTH: 22
<212> TYPE: RNA
<213> ORGANISM: Homo sapiens

<400> SEQUENCE: 45
acuggacuua gggucagaag gc                                              22

<210> SEQ ID NO 46
<211> LENGTH: 21
<212> TYPE: RNA
<213> ORGANISM: Homo sapiens

```
<400> SEQUENCE: 46
acuggacuug gagucagaag g                                              21

<210> SEQ ID NO 47
<211> LENGTH: 22
<212> TYPE: RNA
<213> ORGANISM: Homo sapiens

<400> SEQUENCE: 47
cagcagcaau ucauguuuug aa                                             22

<210> SEQ ID NO 48
<211> LENGTH: 21
<212> TYPE: RNA
<213> ORGANISM: Homo sapiens

<400> SEQUENCE: 48
ucacuccucu ccucccgucu u                                              21

<210> SEQ ID NO 49
<211> LENGTH: 22
<212> TYPE: RNA
<213> ORGANISM: Homo sapiens

<400> SEQUENCE: 49
ucaggcucag uccccucccg au                                             22

<210> SEQ ID NO 50
<211> LENGTH: 22
<212> TYPE: RNA
<213> ORGANISM: Homo sapiens

<400> SEQUENCE: 50
uccuguacug agcugccccg ag                                             22

<210> SEQ ID NO 51
<211> LENGTH: 21
<212> TYPE: RNA
<213> ORGANISM: Homo sapiens

<400> SEQUENCE: 51
cagcagcaca cugugguuug u                                              21

<210> SEQ ID NO 52
<211> LENGTH: 21
<212> TYPE: RNA
<213> ORGANISM: Homo sapiens

<400> SEQUENCE: 52
uuaagacuug cagugauguu u                                              21

<210> SEQ ID NO 53
<211> LENGTH: 23
<212> TYPE: RNA
<213> ORGANISM: Homo sapiens

<400> SEQUENCE: 53
ucggggauca ucaugucacg aga                                            23

<210> SEQ ID NO 54
<211> LENGTH: 22
<212> TYPE: RNA
<213> ORGANISM: Homo sapiens
```

<400> SEQUENCE: 54
uauugcacuu gucccggccu gu                                            22

<210> SEQ ID NO 55
<211> LENGTH: 22
<212> TYPE: RNA
<213> ORGANISM: Homo sapiens

<400> SEQUENCE: 55
uauugcacuc gucccggccu cc                                            22

<210> SEQ ID NO 56
<211> LENGTH: 22
<212> TYPE: RNA
<213> ORGANISM: Homo sapiens

<400> SEQUENCE: 56
ugagguagua gguuguauag uu                                            22

<210> SEQ ID NO 57
<211> LENGTH: 22
<212> TYPE: RNA
<213> ORGANISM: Homo sapiens

<400> SEQUENCE: 57
ugagguagua gguugugugg uu                                            22

<210> SEQ ID NO 58
<211> LENGTH: 22
<212> TYPE: RNA
<213> ORGANISM: Homo sapiens

<400> SEQUENCE: 58
ugagguagua gguuguaugg uu                                            22

<210> SEQ ID NO 59
<211> LENGTH: 22
<212> TYPE: RNA
<213> ORGANISM: Homo sapiens

<400> SEQUENCE: 59
agagguagua gguugcauag uu                                            22

<210> SEQ ID NO 60
<211> LENGTH: 22
<212> TYPE: RNA
<213> ORGANISM: Homo sapiens

<400> SEQUENCE: 60
ugagguagga gguuguauag uu                                            22

<210> SEQ ID NO 61
<211> LENGTH: 22
<212> TYPE: RNA
<213> ORGANISM: Homo sapiens

<400> SEQUENCE: 61
ugagguagua gauuguauag uu                                            22

<210> SEQ ID NO 62
<211> LENGTH: 22
<212> TYPE: RNA
<213> ORGANISM: Homo sapiens -continued

<400> SEQUENCE: 62
ugagguagua guuuguacag uu                                           22

<210> SEQ ID NO 63
<211> LENGTH: 22
<212> TYPE: RNA
<213> ORGANISM: Homo sapiens

<400> SEQUENCE: 63
aaaccguuac cauuacugag uu                                           22

<210> SEQ ID NO 64
<211> LENGTH: 16
<212> TYPE: DNA
<213> ORGANISM: Homo sapiens

<400> SEQUENCE: 64 cttttttgctc gtctta                                                 16

<210> SEQ ID NO 65
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be piperazine modified thymidine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be piperazine modified thymidine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be piperazine modified thymidine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be piperazine modified thymidine
<220> FEATURE:
<221> NAME/KEY: misc_feature
<222> LOCATION: (16)..(16)
<223> OTHER INFORMATION: May be 2'OMe adenosine

```
<400> SEQUENCE: 65 cttttttgctc gtctta                                                        16

<210> SEQ ID NO 66
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be 2'OMe and base modified
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2'OMe and base modified
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2'OMe and base modified
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 2'OMe and base modified
<220> FEATURE:
<221> NAME/KEY: misc_feature
<222> LOCATION: (16)..(16)
<223> OTHER INFORMATION: May be 2'OMe adenosine

<400> SEQUENCE: 66
cuuuuugcuc gucuua                                                         16

<210> SEQ ID NO 67
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages

<400> SEQUENCE: 67 cttttttgctc gtctta                                                        16
```

```
<210> SEQ ID NO 68
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be 2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 68
cuuuuugcuc gucuua                                                       16

<210> SEQ ID NO 69
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be locked nucleic acid cytidine
<220> FEATURE:
<221> NAME/KEY: misc_feature
<222> LOCATION: (5)..(6)
<223> OTHER INFORMATION: May be locked nucleic acid thymidine
<220> FEATURE:
<221> NAME/KEY: misc_feature
<222> LOCATION: (8)..(8)
<223> OTHER INFORMATION: May be locked nucleic acid cytidine
```

```
<220> FEATURE:
<221> NAME/KEY: misc_feature
<222> LOCATION: (10)..(10)
<223> OTHER INFORMATION: May be locked nucleic acid cytidine
<220> FEATURE:
<221> NAME/KEY: misc_feature
<222> LOCATION: (11)..(11)
<223> OTHER INFORMATION: May be locked nucleic acid guanosine
<220> FEATURE:
<221> NAME/KEY: misc_feature
<222> LOCATION: (13)..(13)
<223> OTHER INFORMATION: May be locked nucleic acid cytidine
<220> FEATURE:
<221> NAME/KEY: misc_feature
<222> LOCATION: (15)..(15)
<223> OTHER INFORMATION: May be locked nucleic acid thymidine
<220> FEATURE:
<221> NAME/KEY: misc_feature
<222> LOCATION: (16)..(16)
<223> OTHER INFORMATION: May be locked nucleic acid adenosine

<400> SEQUENCE: 69 cttttgctc gtctta                                                       16

<210> SEQ ID NO 70
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be locked nucleic acid thymidine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be locked nucleic acid thymidine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be locked nucleic acid thymidine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be locked nucleic acid thymidine
<220> FEATURE:
<221> NAME/KEY: misc_feature
<222> LOCATION: (16)..(16)
<223> OTHER INFORMATION: May be 2'OMe adenosine
```

-continued

```
<400> SEQUENCE: 70 cttttttgctc gtctta                                                       16

<210> SEQ ID NO 71
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be benzyl-2'-OMe-uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be benzyl-2'-OMe-uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be benzyl-2'-OMe-uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be benzyl-2'-OMe-uridine
<220> FEATURE:
<221> NAME/KEY: misc_feature
<222> LOCATION: (16)..(16)
<223> OTHER INFORMATION: May be 2'OMe adenosine

<400> SEQUENCE: 71
cuuuuugcuc gucuua                                                        16

<210> SEQ ID NO 72
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be C-6 2'OMe uridine
```

```
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be C-6 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be C-6 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be C-6 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 72
cuuuuugcuc gucuua                                                 16

<210> SEQ ID NO 73
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be 3-propyl-imidazole-2'OMe-uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 3-propyl-imidazole-2'OMe-uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
```

```
<220> FEATURE:
<221> NAME/KEY: misc_feature
<222> LOCATION: (12)..(12)
<223> OTHER INFORMATION: May be 3-propyl-imidazole-2'OMe-uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 3-propyl-imidazole-2'OMe-uridine
<220> FEATURE:
<221> NAME/KEY: misc_feature
<222> LOCATION: (16)..(16)
<223> OTHER INFORMATION: May be 2'OMe adenosine

<400> SEQUENCE: 73
cuuuuugcuc gucuua                                                            16

<210> SEQ ID NO 74
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be 2-ethyl-2-methyl-imidazole-2'OMe-uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2-ethyl-2-methyl-imidazole-2'OMe-uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2-ethyl-2-methyl-imidazole-2'OMe-uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 2-ethyl-2-methyl-imidazole-2'OMe-uridine
<220> FEATURE:
<221> NAME/KEY: misc_feature
<222> LOCATION: (16)..(16)
<223> OTHER INFORMATION: May be 2'OMe adenosine

<400> SEQUENCE: 74
cuuuuugcuc gucuua                                                            16
```

-continued

```
<210> SEQ ID NO 75
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(3)
<223> OTHER INFORMATION: May be 2-ethyl-2-methyl-imidazole-2'OMe-uridine
<220> FEATURE:
<221> NAME/KEY: misc_feature
<222> LOCATION: (4)..(6)
<223> OTHER INFORMATION: May be 2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 2-ethyl-2-methyl-imidazole-2'OMe-uridine
<220> FEATURE:
<221> NAME/KEY: misc_feature
<222> LOCATION: (16)..(16)
<223> OTHER INFORMATION: May be 2'OMe adenosine

<400> SEQUENCE: 75
cuuuuugcuc gucuua                                                       16

<210> SEQ ID NO 76
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be propyl dimethyl amino 2'OMe uridine
```

-continued

```
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be propyl dimethyl amino 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be propyl dimethyl amino 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be propyl dimethyl amino 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 76
cuuuuugcuc gucuua                                                        16

<210> SEQ ID NO 77
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(3)
<223> OTHER INFORMATION: May be propyl dimethyl amino 2'OMe uridine
<220> FEATURE:
<221> NAME/KEY: misc_feature
<222> LOCATION: (4)..(6)
<223> OTHER INFORMATION: May be 2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2'OMe uridine
<220> FEATURE:
<221> NAME/KEY: misc_feature
<222> LOCATION: (10)..(10)
<223> OTHER INFORMATION: May be 2'OMe cytidine
```

<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be propyl dimethyl amino 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 77
cuuuuugcuc gucuua                                                          16

<210> SEQ ID NO 78
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be propyl morpholino 2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be propyl morpholino 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be propyl morpholino 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be propyl morpholino 2'OMe uridine
<220> FEATURE:
<221> NAME/KEY: misc_feature
<222> LOCATION: (16)..(16)
<223> OTHER INFORMATION: May be 2'OMe adenosine

```
<400> SEQUENCE: 78
cuuuuugcuc gucuua                                                 16

<210> SEQ ID NO 79
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(6)
<223> OTHER INFORMATION: May be C-18 2'OMe uridine or propyl morpholino
      2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be C-18 2'OMe uridine or propyl morpholino
      2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be C-18 2'OMe uridine or propyl morpholino
      2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(14)
<223> OTHER INFORMATION: May be C-18 2'OMe uridine or propyl morpholino
      2'OMe uridine
<220> FEATURE:
<221> NAME/KEY: misc_feature
<222> LOCATION: (15)..(15)
<223> OTHER INFORMATION: May be C-18 uridine
<220> FEATURE:
<221> NAME/KEY: misc_feature
<222> LOCATION: (16)..(16)
<223> OTHER INFORMATION: May be 2'OMe adenosine

<400> SEQUENCE: 79
cuuuuugcuc gucuua                                                 16

<210> SEQ ID NO 80
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
```

```
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(3)
<223> OTHER INFORMATION: May be propyl morpholino 2'OMe uridine
<220> FEATURE:
<221> NAME/KEY: misc_feature
<222> LOCATION: (4)..(6)
<223> OTHER INFORMATION: May be 2'OMe uridine
<220> FEATURE:
<221> NAME/KEY: misc_feature
<222> LOCATION: (7)..(7)
<223> OTHER INFORMATION: May be 2'OMe guanosine
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be propyl morpholino 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 80
cuuuuugcuc gucuua                                                     16

<210> SEQ ID NO 81
<211> LENGTH: 16
<212> TYPE: RNA
<213> ORGANISM: Homo sapiens
<220> FEATURE:
<221> NAME/KEY: misc_feature
<222> LOCATION: (1)..(16)
<223> OTHER INFORMATION: May be joined by phosphorothioate linkages
<220> FEATURE:
<221> NAME/KEY: misc_feature
<222> LOCATION: (1)..(1)
<223> OTHER INFORMATION: May be 2'OMe cytidine
<220> FEATURE:
<221> NAME/KEY: misc_feature
<222> LOCATION: (2)..(3)
<223> OTHER INFORMATION: May be 2'OMe uridine
<220> FEATURE:
<221> NAME/KEY: misc_feature
<222> LOCATION: (4)..(6)
<223> OTHER INFORMATION: May be propyl morpholino 2'OMe uridine
<220> FEATURE:
<221> NAME/KEY: misc_feature
<222> LOCATION: (7)..(7)
<223> OTHER INFORMATION: May be 2'OMe guanosine
```

```
<220> FEATURE:
<221> NAME/KEY: misc_feature
<222> LOCATION: (8)..(8)
<223> OTHER INFORMATION: May be 2'OMe cytidine
<220> FEATURE:
<221> NAME/KEY: misc_feature
<222> LOCATION: (9)..(9)
<223> OTHER INFORMATION: May be propyl morpholino 2'OMe uridine
<220> FEATURE:
<221> NAME/KEY: misc_feature
<222> LOCATION: (10)..(10)
<223> OTHER INFORMATION: May be 2'OMe cytidine
<220> FEATURE:
<221> NAME/KEY: misc_feature
<222> LOCATION: (11)..(11)
<223> OTHER INFORMATION: May be 2'OMe guanosine
<220> FEATURE:
<221> NAME/KEY: misc_feature
<222> LOCATION: (12)..(12)
<223> OTHER INFORMATION: May be propyl morpholino 2'OMe uridine
<220> FEATURE:
<221> NAME/KEY: misc_feature
<222> LOCATION: (13)..(13)
<223> OTHER INFORMATION: May be 2'OMe cytidine
<220> FEATURE:
<221> NAME/KEY: misc_feature
<222> LOCATION: (14)..(15)
<223> OTHER INFORMATION: May be 2'OMe uridine
<220> FEATURE:
<221> NAME/KEY: misc_feature
<222> LOCATION: (16)..(16)
<223> OTHER INFORMATION: May be 2'OMe adenosine

<400> SEQUENCE: 81
cuuuuugcuc gucuua                                              16
```